US009820838B2

(12) United States Patent
Liu et al.

(10) Patent No.: US 9,820,838 B2
(45) Date of Patent: *Nov. 21, 2017

(54) SINGLE PLANE TISSUE REPAIR PATCH

(71) Applicant: Ethicon, Inc., Somerville, NJ (US)

(72) Inventors: Xiaodong Liu, Hillsborough, NJ (US); Michael Cardinale, Morristown, NJ (US)

(73) Assignee: Ethicon, Inc., Somerville, NJ (US)

( * ) Notice: Subject to any disclaimer, the term of this patent is extended or adjusted under 35 U.S.C. 154(b) by 47 days.

This patent is subject to a terminal disclaimer.

(21) Appl. No.: 13/793,281

(22) Filed: Mar. 11, 2013

(65) Prior Publication Data

US 2013/0267971 A1 Oct. 10, 2013

(51) Int. Cl.
*A61F 2/00* (2006.01)

(52) U.S. Cl.
CPC .... *A61F 2/0063* (2013.01); *A61F 2002/0068* (2013.01); *A61F 2230/0008* (2013.01); *A61F 2250/0031* (2013.01); *A61F 2250/0051* (2013.01)

(58) Field of Classification Search
CPC ............ A61F 2/0063; A61F 2002/0071; A61F 2002/0081; A61F 2002/0086; A61F 2002/009; A61F 2002/0068; A61F 2002/0072; A61B 17/0057; A61B 2017/00641
USPC ........................ 606/151, 213, 215; 623/23.72
See application file for complete search history.

(56) References Cited

U.S. PATENT DOCUMENTS

| | | | |
|---|---|---|---|
| 5,176,692 A | 1/1993 | Wilk |
| 5,258,000 A | 11/1993 | Gianturco |
| 5,593,441 A | 1/1997 | Lichtenstein |
| 5,634,931 A | 6/1997 | Kugel |
| 5,686,090 A | 11/1997 | Schilder |
| 5,716,409 A | 2/1998 | Debbas |
| 5,743,917 A | 4/1998 | Saxon |
| 5,769,864 A | 6/1998 | Kugel |
| 5,861,003 A | 1/1999 | Latson |
| 6,066,776 A | 5/2000 | Goodwin |
| 6,066,777 A | 5/2000 | Benchetrit |
| 6,113,623 A | 9/2000 | Sgro |
| 6,120,539 A | 9/2000 | Eldridge |
| 6,171,318 B1 | 1/2001 | Kugel |
| 6,224,616 B1 | 5/2001 | Kugel |

(Continued)

FOREIGN PATENT DOCUMENTS

| | | |
|---|---|---|
| CN | 2590576 Y | 12/2003 |
| DE | 19832634 A1 | 1/2000 |

(Continued)

OTHER PUBLICATIONS

Saburo Kakizoe, et al. "Flexible Tack for Ventral Hernia Repair", Surg Today (2011) 41: pp. 1024-1025.

*Primary Examiner* — Ryan J Severson
(74) *Attorney, Agent, or Firm* — E. Richard Skula

(57) ABSTRACT

A novel single plane tissue repair device such as a patch is disclosed. The device has a base member with an opening therethrough, and a closure member associated with the opening. The mesh has a biaborbable polymeric adhesion barrier attached to the bottom side of the base member about its periphery to form a pocket that is accessible through the opening. The mesh may be used in open surgical procedures for hernia repairs and other repairs of body wall defects.

39 Claims, 33 Drawing Sheets

(56) References Cited

U.S. PATENT DOCUMENTS

| | | |
|---|---|---|
| 6,241,768 B1 | 6/2001 | Agarwal |
| 6,258,124 B1 | 7/2001 | Darois |
| 6,270,530 B1 | 8/2001 | Eldridge |
| 6,290,708 B1 | 9/2001 | Kugel |
| 6,319,264 B1 | 11/2001 | Törmälä |
| 6,383,201 B1 | 5/2002 | Dong |
| 6,391,060 B1 | 5/2002 | Ory |
| 6,551,356 B2 | 4/2003 | Rousseau |
| 6,565,580 B1 | 5/2003 | Beretta |
| 6,610,006 B1 | 8/2003 | Amid |
| 6,652,595 B1 | 11/2003 | Nicolo |
| 6,669,735 B1 | 12/2003 | Pelissier |
| 6,723,133 B1 | 4/2004 | Pajotin |
| 6,736,854 B2 | 5/2004 | Vadurro |
| 6,790,213 B2 | 9/2004 | Cherok |
| 6,800,082 B2 | 10/2004 | Rousseau |
| 6,824,420 B2 | 11/2004 | Ushiro |
| 7,101,381 B2 | 9/2006 | Ford |
| 7,156,804 B2 | 1/2007 | Nicolo |
| 7,404,819 B1 | 7/2008 | Darios |
| 7,785,334 B2 | 8/2010 | Ford |
| 7,789,888 B2 | 9/2010 | Bartee |
| 7,806,905 B2 | 10/2010 | Ford |
| 7,824,420 B2 | 11/2010 | Eldridge |
| 7,828,854 B2 * | 11/2010 | Rousseau et al. ......... 623/23.72 |
| 7,879,108 B2 | 2/2011 | Vadurro |
| 8,617,206 B2 * | 12/2013 | Sargeant et al. ............ 606/213 |
| 2003/0004581 A1 | 1/2003 | Rousseau |
| 2003/0040809 A1 | 2/2003 | Goldmann |
| 2003/0078602 A1 | 4/2003 | Rousseau |
| 2003/0130745 A1 * | 7/2003 | Cherok et al. ............. 623/23.72 |
| 2003/0212461 A1 * | 11/2003 | Vadurro et al. ............ 623/23.64 |
| 2004/0215219 A1 | 10/2004 | Eldridge |
| 2005/0043716 A1 | 2/2005 | Frimer |
| 2005/0192600 A1 | 9/2005 | Nicolo |
| 2005/0244455 A1 | 11/2005 | Greenawalt |
| 2005/0288691 A1 | 12/2005 | Leiboff |
| 2005/0288775 A1 | 12/2005 | Dong |
| 2006/0015143 A1 | 1/2006 | Alvarado |
| 2006/0064175 A1 | 3/2006 | Pelissier |
| 2006/0253203 A1 | 11/2006 | Alvarado |
| 2007/0088391 A1 | 4/2007 | McAlexander |
| 2007/0260179 A1 | 11/2007 | Sholev |
| 2007/0260268 A1 | 11/2007 | Bartee |
| 2007/0276178 A1 | 11/2007 | Carteron |
| 2007/0299538 A1 * | 12/2007 | Roeber ...................... 623/23.72 |
| 2008/0033461 A1 | 2/2008 | Koeckerling |
| 2008/0109017 A1 | 5/2008 | Herweck |
| 2008/0147099 A1 | 6/2008 | Uen |
| 2008/0167729 A1 | 7/2008 | Nelson |
| 2008/0172071 A1 | 7/2008 | Barker |
| 2008/0243149 A1 | 10/2008 | Kockerling |
| 2008/0255593 A1 | 10/2008 | St-Germain |
| 2008/0269896 A1 | 10/2008 | Cherok |
| 2008/0306497 A1 | 12/2008 | Brown |
| 2009/0099579 A1 | 4/2009 | Nentwick |
| 2009/0157195 A1 | 6/2009 | Siedle |
| 2009/0192532 A1 | 7/2009 | Spinnler |
| 2009/0254103 A1 | 10/2009 | Deutsch |
| 2009/0259235 A1 | 10/2009 | Doucet |
| 2009/0264919 A1 * | 10/2009 | Sater et al. .................... 606/213 |
| 2010/0286716 A1 * | 11/2010 | Ford et al. .................... 606/151 |
| 2010/0292718 A1 | 11/2010 | Sholev |
| 2010/0298953 A1 | 11/2010 | Holzman |
| 2010/0305589 A1 | 12/2010 | Solecki |
| 2011/0004306 A1 | 1/2011 | Harper |
| 2011/0018227 A1 | 1/2011 | Thorpe |
| 2011/0060420 A1 | 3/2011 | Bartee |
| 2011/0144667 A1 | 6/2011 | Horton |
| 2011/0184441 A1 | 7/2011 | St-Germain |
| 2011/0224704 A1 | 9/2011 | Bailly |
| 2011/0295283 A1 | 12/2011 | Darois |
| 2012/0010635 A1 | 1/2012 | Yeretsian |
| 2012/0027804 A1 | 2/2012 | Odermatt |
| 2012/0065463 A1 | 3/2012 | Adzich |
| 2012/0179175 A1 * | 7/2012 | Hammell ...................... 606/151 |
| 2012/0253366 A1 * | 10/2012 | Darois ................. A61F 2/0063 |
| | | 606/151 |
| 2013/0218125 A1 * | 8/2013 | Stopek et al. ................ 604/500 |

FOREIGN PATENT DOCUMENTS

| | | |
|---|---|---|
| EP | 783270 A1 | 7/1997 |
| EP | 783270 A4 | 7/1998 |
| EP | 1317227 A1 | 6/2003 |
| EP | 1384450 A1 | 1/2004 |
| EP | 783270 B1 | 6/2004 |
| EP | 1454599 A2 | 9/2004 |
| EP | 1467677 A1 | 10/2004 |
| EP | 1317227 B1 | 11/2004 |
| EP | 1454599 A3 | 2/2006 |
| EP | 1467677 B1 | 4/2007 |
| EP | 1797842 A1 | 6/2007 |
| EP | 1797842 B1 | 12/2008 |
| EP | 2002801 A1 | 12/2008 |
| EP | 2072023 A1 | 6/2009 |
| EP | 2002801 B1 | 6/2010 |
| EP | 2586400 A1 | 5/2013 |
| EP | 2586401 A1 | 5/2013 |
| EP | 2586607 A1 | 5/2013 |
| WO | WO0219916 A1 | 3/2002 |
| WO | WO2004103212 A1 | 12/2004 |
| WO | WO2006066882 A2 | 6/2006 |
| WO | WO2008002549 A2 | 1/2008 |
| WO | WO2008101690 A2 | 8/2008 |
| WO | WO2008002549 A3 | 10/2008 |
| WO | WO2008101690 A3 | 11/2008 |
| WO | WO2009003726 A1 | 1/2009 |
| WO | WO2009050890 A1 | 4/2009 |
| WO | WO2010005923 A1 | 1/2010 |
| WO | WO2010039978 A2 | 4/2010 |
| WO | WO2010071624 A1 | 6/2010 |
| WO | WO2010039978 A3 | 8/2010 |
| WO | WO2010088699 A2 | 8/2010 |
| WO | WO2010129641 A1 | 11/2010 |
| WO | WO2011003422 A1 | 1/2011 |

* cited by examiner

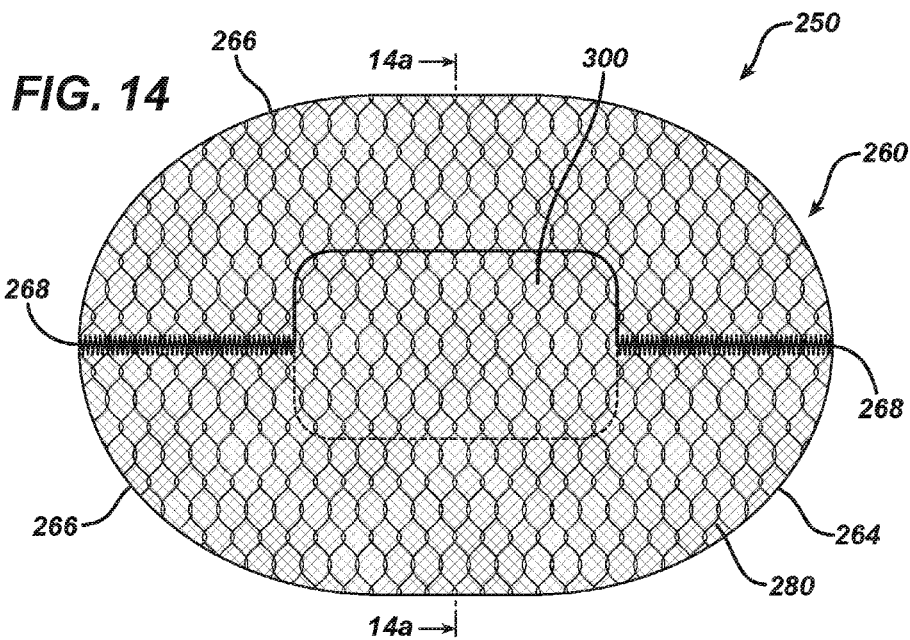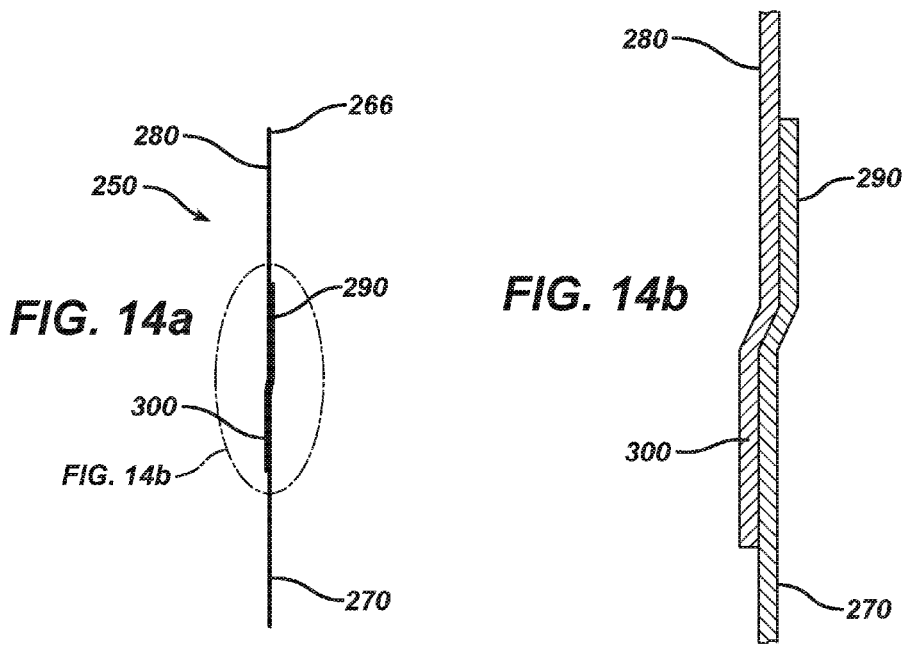

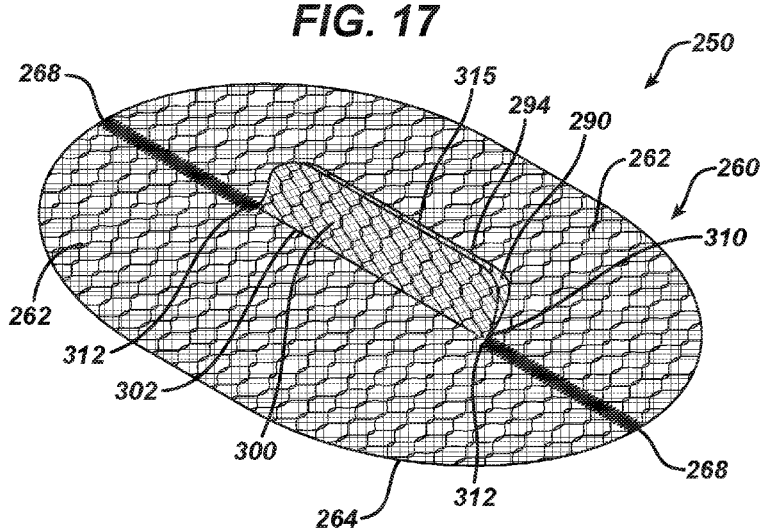
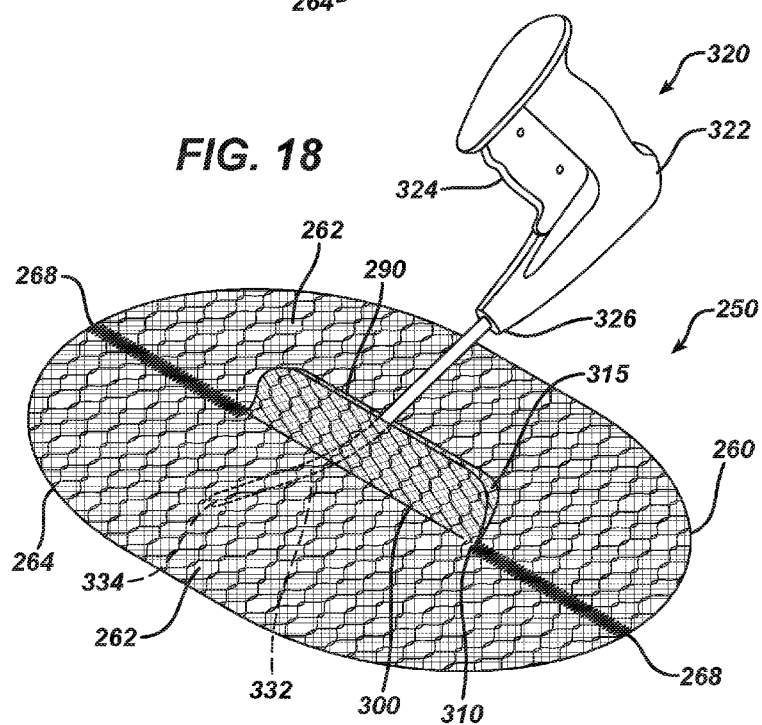

SINGLE PLANE TISSUE REPAIR PATCH

REFERENCE TO RELATED APPLICATIONS

This is a continuation-in-part of co-pending commonly assigned U.S. patent application Ser. No. 13/443,347 filed on Apr. 10, 2012, which is incorporated by reference.

TECHNICAL FIELD

The field of art to which this invention pertains is implantable surgical tissue repair patches, more particularly implantable surgical mesh hernia patches for use in hernia repair procedures.

BACKGROUND OF THE INVENTION

Hernia repair is a relatively straightforward surgical procedure, the ultimate goal of which is to restore the mechanical integrity of the abdominal wall by repairing a muscle wall defect through which the peritoneum and possibly a section of the underlying viscera has protruded. There are various types of hernias, each with its own specific surgical repair procedure, including ventral hernias, umbilical hernias, incisional hernias, sports hernias, femoral hernias, and inguinal hernias. It is believed that most hernias are attributable to a weakness in sections of the tissues of the abdominal wall.

Precipitating events, such as unusual movements or lifting extremely heavy weights, may cause the weak spots in the abdominal wall tissue to be excessively stressed, resulting in tissue separation or rupture and protrusion of a section of peritoneum and underlying viscera, e.g., intestine, through the separated or ruptured tissue section. This weakness may be attributable to several factors. Weakness in the abdominal wall may be congenital or may be associated with a prior incision from a surgical procedure or a trocar wound. Other factors may include trauma, genetic predisposition, and aging.

Even though the commonly used, conventional surgical procedures for correcting or repairing the various types of hernias are somewhat specific, there is a commonality with respect to the mechanical repair. Typically, the protrusion of the peritoneum through a muscle or abdominal wall defect results in a hernia sack containing the underlying and protruding viscera. The hernia sack is dissected and the viscera are pushed back into the abdominal cavity. Then, a tissue reinforcing or repair implant such a mesh patch device is typically implanted and secured at the site of the abdominal wall defect. Autologous tissue quickly grows into the mesh implant, providing the patient with a secure and strong repair. In certain patient presentations, it may be desirable to suture or otherwise close the defect without an implant, although this is typically much less desirable for the optimal outcome.

One common type of hernia is a ventral hernia. This type of hernia typically occurs in the abdominal wall and may be caused by a prior incision or puncture, or by an area of tissue weakness that is stressed. There are several repair procedures that can be employed by the surgeon to treat such hernias, depending upon the individual characteristics of the patient and the nature of the hernia. In one technique, an onlay mesh is implanted on the dorsal surface of the anterior fascia of the abdominal wall. Another technique provides for an inlay mesh, where the prosthetic material is sutured to the abdominal wall and acts as a "bridge" to close the abdominal defect. Placement of a prosthetic mesh posterior to the rectus muscle of the abdominal wall is known as the Reeves Stoppa or retromuscular technique. In this technique, a mesh implant is located beneath the muscle of the abdominal wall but above the peritoneum. Implantation of the mesh in the intra-peritoneal location can be done via an open or laparoscopic approach. The mesh is inserted into the patient's abdominal cavity through an open anterior incision or via a trocar and positioned to cover the defect. The surgeon then fixates the mesh implant to the abdominal wall with conventional mechanical fixation or with sutures placed through the full thickness of the abdominal wall. There are a variety of such mechanical fixation devices that can be used in laparoscopic or open surgery, e.g., tacking instruments. Intraperitoneal placement of mesh via an open approach may be the desired technique of repair where the layers of the abdominal wall are attenuated and a laparoscopic approach is not desired. Placement of mesh via this technique presents several unique challenges including poor visibility during mesh handling and fixation, poor handling, and deficient ergonomics of the currently available products. Mesh repair patch implants designed for intraperitoneal placement typically requires an additional treatment or layer to function as a tissue separating component to separate the viscera from the prosthetic abdominal wall repair layer, and thereby prevent or substantially inhibit the formation of post-operative adhesions. The addition of this layer may add to the complexity of wound healing due to the presence and mass of an additional layer.

Although hernia repair patch implants exist for open ventral hernia repairs, there are deficiencies known to be associated with their use. The deficiencies include difficulty in handling the mesh, poor visibility during mesh handling, implantation and fixation, poor usability and ergonomics when using a laparoscopic instrument, and the use of dual or multiple layers of mesh. The commercially available meshes repair patch implants for this application typically have at least dual layers of mesh or fabric with pockets or skirts to provide for affixation to the parietal wall via the top layer or skirt. It can also be appreciated that multiple layer meshes introduce more foreign body mass and tend to be more expensive and complicated to manufacture than a single layer mesh implant Accordingly, there is a need in this art for novel tissue repair implants, such as ventral hernia repair patch implants, that can be used in an open surgical procedure, and which do not require a mesh anchoring or affixation layer, and which may be secured to tissue using a single or multiple crown technique.

SUMMARY OF THE INVENTION

Accordingly, novel tissue repair patches are disclosed. The tissue repair patches have a substantially flat or planar base member. The base member is preferably a mesh. There is an opening located in the base member, and, there is a closure member associated with the opening. The base member has a top side and a bottom side. The patch may have a polymeric layer on at least part of at least one side of the base member. It is preferred that the side of the mesh that faces the viscera has a polymeric layer covering substantially all of that side. The tissue repair patch has a bioabsorbable adhesion barrier member attached about its periphery to the periphery of the bottom side of the base member to form a pocket accessible through the opening. The tissue repair patches of the present invention are especially useful in an open hernia repair procedure, such as a ventral hernia repair, and are also useful in other types of body wall tissue repairs.

Another aspect of the present invention is a method of repairing a body wall defect, such as a hernia defect, in an open surgical procedure using the above-described tissue repair patch implants.

These and other aspects and advantages of the present invention will become more apparent from the following description and accompanying drawings.

BRIEF DESCRIPTION OF THE DRAWINGS

FIG. 14 is a plan view of a preferred embodiment of a tissue repair patch of the present invention; the patch is seen to have a pair of closure flap members.

FIG. 14a is a cross-sectional view of the repair patch of FIG. 14 along View Line 14a-14a.

FIG. 14b is a magnified partial view of the cross-section of FIG. 14a. illustrating the flaps positioned about the opening in the base member of the patch.

FIG. 17 is a perspective view of the tissue repair mesh patch of FIG. 16; both closure flaps are in the up position such that the opening in the base member is accessible between the flaps.

FIG. 18 is a perspective view of the mesh repair patch of FIG. 17, illustrating the distal end of a curved elongated shaft of a surgical tacking instrument partially inserted through the opening of the base member in a position below the patch to secure the mesh repair patch to tissue.

FIG. 34 is a partial cross-sectional view of a repair patch of the present invention in which the adhesion barrier is attached to the top side of the base member of the patch about the periphery of the base member.

DETAILED DESCRIPTION OF THE INVENTION

Figure 1:
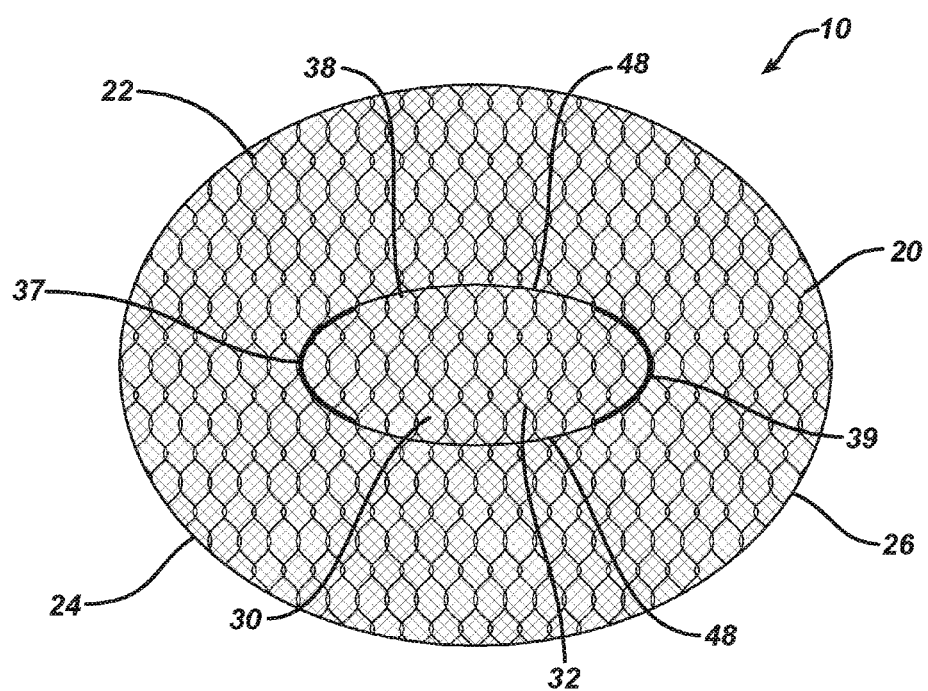
FIG. 1 is a plan view of an embodiment of a single plane tissue repair mesh patch of the present invention; the patch has a base member having an opening, and a closure patch member mounted to the top side of the base member over the opening.

The novel tissue repair patches or devices of the present invention are particularly useful in open ventral or incisional hernia repair surgical procedures. The tissue repair patch devices consist of a base member having an opening. The base member has a closure member or device associated with the opening for securing the opening after implantation. The repair patch devices of the present invention have utility in other conventional tissue repair procedures including inguinal hernia repair procedures, trocar puncture wounds, trocar incisional hernias, etc.

Tissue repair implants and surgical instruments for applying tacks to fixate tissue repair implants are disclosed in the following commonly assigned, co-pending patent applications, which are incorporated by reference: U.S. Ser. Nos. 12/464,151; 12/464,165; 12/464,177; 12/464,143; 12/944,651; and 12/815,275.

The tissue repair patches of the present invention may be made from any conventional biocompatible materials. The patches and their components are preferably made from conventional biocompatible polymers that may be nonabsorbable or bioabsorbable. The term bioabsorbable is defined to have its conventional meaning and includes both biodegradable and bioresorbable. Examples of such nonabsorbable polymers include polypropylene, polyester, nylon, ultra high molecular weight polyethylene, and the like and combinations thereof. Examples of suitable bioabsorbable polymers include polylactides (PLA), polyglycolides (PGA), polydioxanones (PDO, PDS), copolymers of PGA/trimethylene carbonate (TMC), copolymers of PLA/TMC, and the like. If desired, combinations of biocompatible nonabsorbable polymers and bioabsorbable polymers may be utilized to construct the tissue repair implant patch devices of the present invention.

Although it is preferred to use surgical meshes to construct the hernia repair patches of the present invention, other conventional woven or nonwoven surgical repair fabrics or thermally formed implants may also be used. In addition, the tissue repair patches may be made from other conventional implantable materials such as PTFE (polytetrafluoroethylene), e.g., ePTFE films and laminates. The patches may consist of composites of polymeric films and meshes, and/or fabrics.

The meshes useful in the hernia repair patch devices of the present invention will be manufactured in a conventional manner using conventional manufacturing equipment and methods including knitting, weaving, non-woven techniques, and the like. The meshes will typically have a pore size sufficient to effectively provide for tissue ingrowth; for example, they may have pore sizes in the range of about 0.3 mm to about 5 mm, and other conventional size ranges. Examples of commercially available nonabsorbable and bioabsorbable polymeric meshes that may be used to construct the hernia repair patches of the present invention include ETHICON PHYSIOMESH™ and ETHICON PROCEED™ Surgical Mesh, available from Ethicon, Inc., Route 22 West Somerville, N.J. 08876.

When constructing the novel tissue repair patches of the present invention from surgical fabrics other than meshes, the fabrics will have open pores with a pore size sufficient to effectively provide for tissue ingrowth; for example, with a typical size of about 0.3 mm to about 3 mm. By "open pores" is meant openings that extend from one side of the fabric to the opposed side, providing a pathway through the fabric. The fabric repair members may be constructed from monofilaments, multifilaments, or combinations thereof. Examples of commercially available non-mesh fabrics that can be used to manufacture the hernia repair patches of the present invention include woven fabrics, textiles and tapes for surgical applications. Other fabrics or materials include perforated condensed ePTFE films and nonwoven fabrics having pore sizes of at least one millimeter. The non-mesh fabrics may be constructed of conventional biocompatible materials.

The fabric or mesh may contain, in addition to a long-term stable polymer, a resorbable polymer (i.e., bioabsorbable or biodegradable). The resorbable and the long-term stable polymer preferably contain monofilaments and/or multifilaments. The terms resorbable polymers and bioabsorbable polymers are used interchangeably herein. The term bioabsorbable is defined to have its conventional meaning. Although not preferred, the fabric or mesh tissue repair member may be manufactured from a bioabsorbable polymer or bioabsorbable polymers without any long-term stable polymers.

The tissue repair patches of the present invention may also include polymer films. The films may be attached to the top surface, the bottom surface or both surfaces and may also cover the peripheral edges of the repair patch devices or extend beyond the periphery of the repair patch devices. The films that are used to manufacture the tissue repair patch implant devices of the present invention will have a thickness that is sufficient to effectively prevent adhesions from forming, or otherwise function as a tissue barrier or tissue separating structure or membrane. For example, the thickness may typically range from about 1 μm to about 500 μm, and preferably from about 5 μm to about 50 μm, however this will depend upon the individual characteristics of the selected polymeric films. The films suitable for use with the repair patches of the present invention include both bioabsorbable and nonabsorbable films. The films are preferably polymer-based and may be made from various conventional biocompatible polymers, including bioabsorbable and nonabsorbable polymers. Non-resorbable or very slowly resorbable substances include polyalkenes (e.g., polypropylene or polyethylene), fluorinated polyolefins (e.g., polytetrafluoroethylene or polyvinylidene fluoride), polyamides, polyurethanes, polyisoprenes, polystyrenes, polysilicones, polycarbonates, polyarylether ketones (PEEKs), polymethacrylic acid esters, polyacrylic acid esters, aromatic polyesters, polyimides as well as mixtures and/or co-polymers of these substances. Also useful are synthetic bioabsorbable polymer materials for example, polyhydroxy acids (e.g., polylactides, polyglycolides, polyhydroxybutyrates, polyhydroxyvalerates), polycaprolactones, polydioxanones, synthetic and natural oligo- and polyamino acids, polyphosphazenes, polyanhydrides, polyorthoesters, polyphosphates, polyphosphonates, polyalcohols, polysaccharides, and polyethers. However, naturally occurring materials such as collagen, gelantin or natural-derived materials such as bioabsorbable Omega 3 fatty acid cross-linked gel films or oxygenated regenerated cellulose (ORC) can also be used.

The films used in the tissue repair patch devices of the present invention may cover the entire outer surfaces of the hernia patch member or a part thereof. In some cases, it is beneficial to have films overlapping the borders and/or peripheries of the repair patches. The repair patches of the present invention may also have adhesion barrier layers attached to one or both sides. The adhesion barriers will typically consist of conventional biocompatible polymeric materials including but not limited to absorbable and nonabsorbable polymers. Examples of conventional nonabsorbable polymeric materials useful for adhesion barriers include expanded polytetrafluoroethylene, polytetrafluoroethylene, silicone, and the like. Examples of conventional absorbable polymeric materials useful for adhesion barriers include oxidized regenerated cellulose, poliglecaprone 25 (copolymer of glycolide and epsilon-caprolactone), and the like.

It is particularly preferred that the tissue repair patches of the present invention have a mesh construction, and the embodiments illustrated in the Figures have such a mesh construction. The tissue repair implants of the present invention have particular utility for hernia repair procedures, but may be used in other tissue repair surgical procedures as well.

Figure 2:
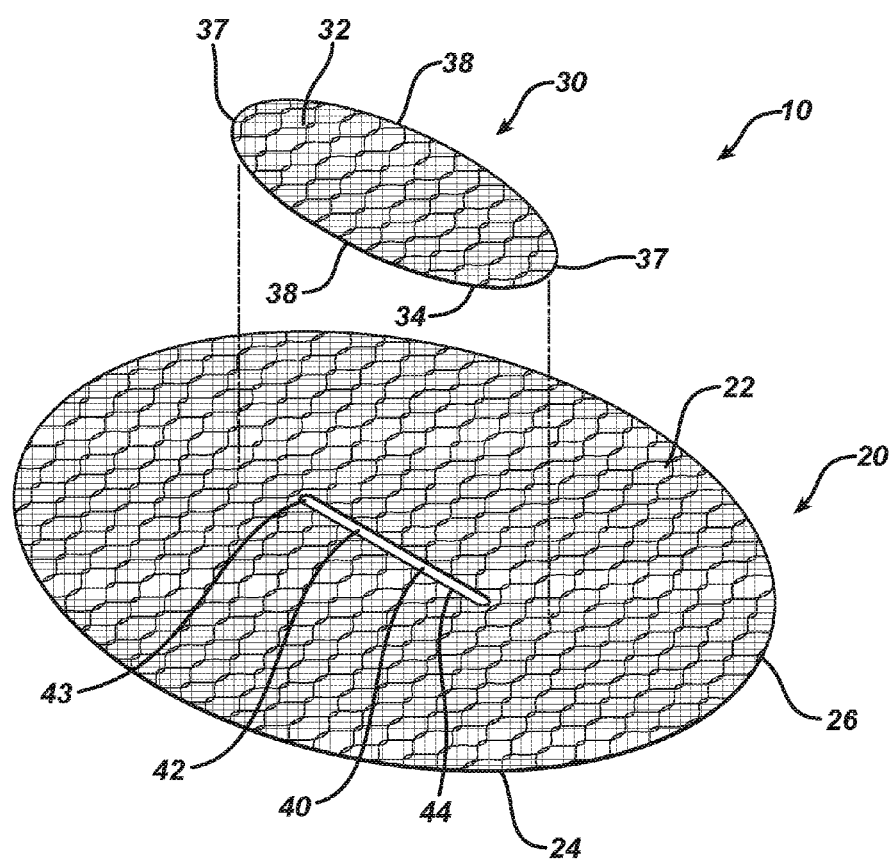
FIG. 2 is an exploded perspective view of the repair mesh patch of FIG. 1.
Figure 3:
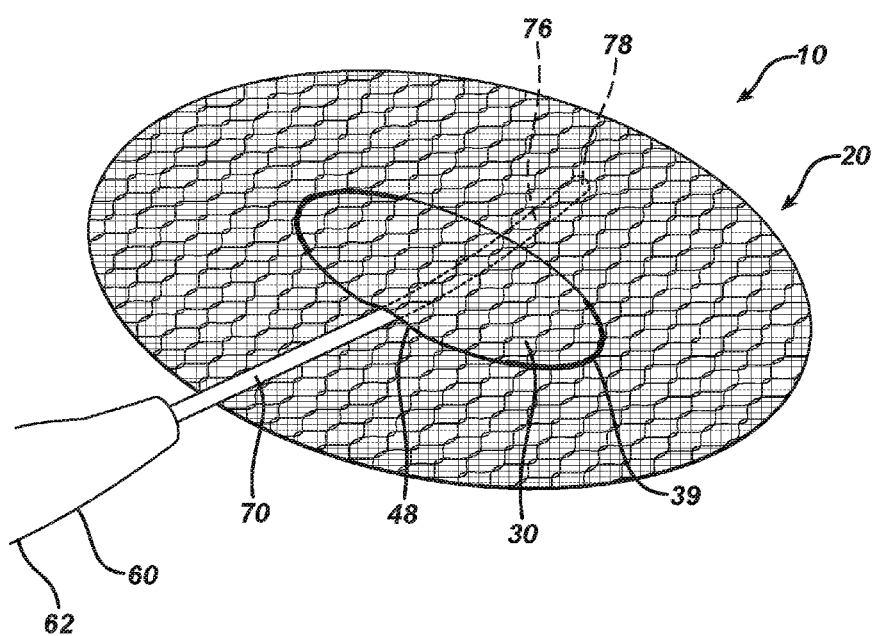
FIG. 3 is an illustration showing a surgical tacking instrument having an elongated shaft partially inserted underneath the flap member and through the opening of the base member of the repair patch of FIG. 1; the instrument shaft is seen as having access to the bottom side of the base member.

Referring now to FIGS. 1-3, a tissue repair patch 10 of the present invention is seen. The patch 10 has a mesh construction. The repair patch 10 is seen to have substantially flat or planar base member 20 and closure patch member 30. The base member 20 is illustrated having a substantially oval shape or configuration, but may have other configurations including square, rectangular, circular, polygonal, etc., combinations thereof and the like. The base member 20 is seen to have top side 22, bottom side 24, and periphery 26. Extending through the base member 20 is the slot 40 having opening 42 bounded by opposed sides 44 and opposed ends 43. The closure patch member 30 is seen to be a substantially flat or planar member having a substantially oval configuration. The closure patch member 30 is seen to have top side 32, bottom side 34, and periphery 35. Closure patch member 30 is seen to have opposed curved ends 37 and opposed sides 38. Patch member 30 is mounted to the top of base member 20 via connections 39 along the ends 37 such that the bottom side 34 of closure patch 30 is adjacent to the top side 22 of base member 20. The closure patch is mounted using any conventional affixation method to create the connections 39, including but not limited to sewing, welding, tacking, riveting, stapling, gluing, etc., and the like. The closure patch 30 is mounted to the base member 20 to cover the slot 40 and opening 42. Openings 48 adjacent to sides 38 provide access passages for surgical instruments to and through opening 42 of slot 40. A partial schematic of a surgical tacking instrument 60 which can be used to tack the base member 20 of patch 10 to tissue is seen in FIG. 3. The instrument 60 has proximal handle 62 and distally extending elongated shaft 70 having distal end 78. A distal section 76 of the shaft 70 is seen to extend through opening 48, underneath the bottom side 34 of closure flap 30 and through opening 42 of slot 40 such that it is positioned below the bottom side 24 of base member 20. The distal end 78 is seen to be positioned in proximity to the periphery 26 of the base member 20 adjacent to bottom side 24 so that surgical tacks may be fired to secure the patch to tissue adjacent to the top side 22 of base member 20 and the top side 32 of closure patch member 30. The repair patch 10 is fixated around its perimeter 26 to tissue with fixation points placed, for example, about every 1 to 2 cm, i.e., the fixation devices or tacks are separated by about 1 cm to 2 cm distances. Although in many embodiments of the tissue or hernia repair patches of the present invention it is preferred to have a slot in the base member to provide an opening through the base member, the opening may be a slit or other types of openings having different geometric configurations may be utilized including circular, oval, rectangular, polygonal, etc., combinations thereof and the like. Although not preferred, it is possible to form the tissue repair patches of the present invention such that the base member and/or closure member are curved or otherwise in more than one plane.

Once the tissue repair patch 10 of the present invention has been implanted and secured to tissue by tacking or other conventional methods (e.g., stapling, suturing, etc.), the shaft section 76 of surgical affixation instrument 60 is removed from the body through the slot 40. The closure patch member 30 prevents underlying tissue or viscera from moving through the slot 40 and opening 42.

Figure 4:
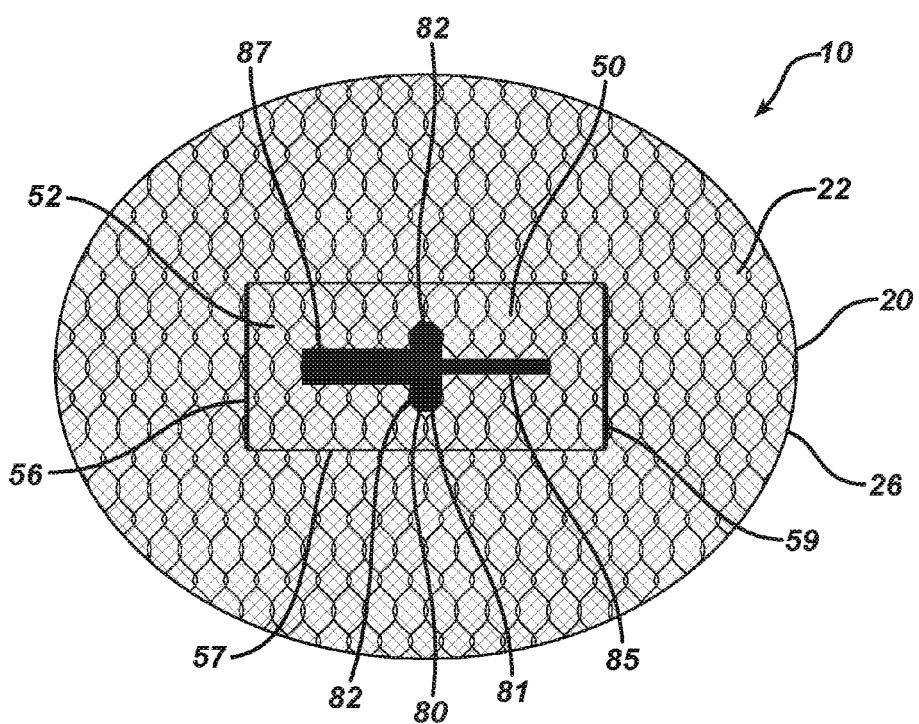
FIG. 4 is a plan view of a tissue repair patch of the present invention that is similar to the repair patch shown in FIG. 1, but which has a rectangular closure patch member connected along its opposed minor sides; the closure patch member is seen to contain a direction guide for use by the surgeon in orienting the patch during implantation.
Figure 5:
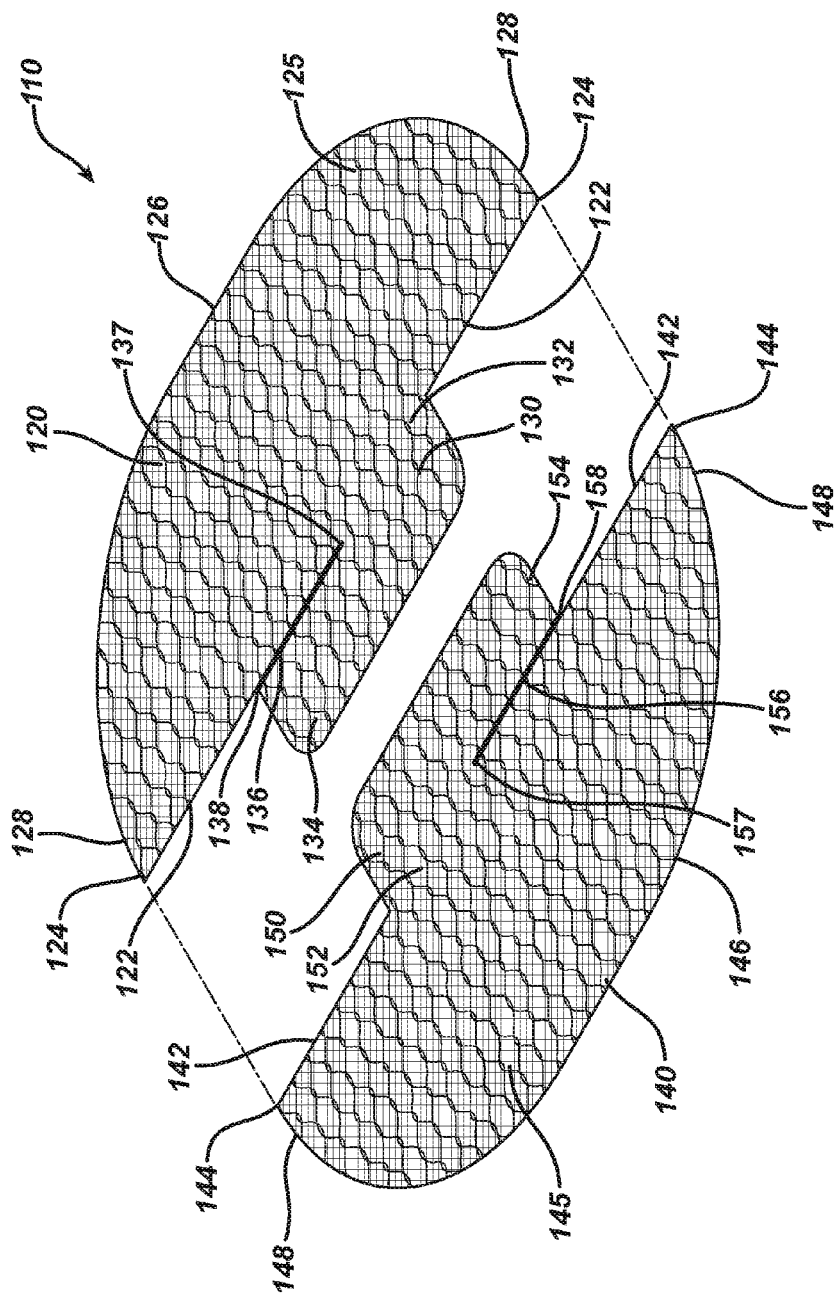
FIG. 5 is an exploded perspective view illustrating two halves of another embodiment of a tissue repair patch of the present invention; the two halves are connected to form a repair mesh patch having closure flaps.

An alternative embodiment of the tissue repair patch 10 is seen in FIG. 4. The patch 10 is seen to have similarly shaped base member 20, however the closure member 50 is seen to have a substantially rectangular shape with opposed minor end sides 56 and opposed major sides 57. Closure member 50 has top side 52 and bottom side 54 adjacent to top side 22 of base member 20. The patch member 50 is mounted to base member 20 over slot 40 by connections 59 along minor sides 56. The connections may be made as described previously. Openings 48 beneath sides 57 provide access to slot 40 and opening 42. As seen in FIG. 4, the tissue repair patch 10 is seen to have a directional indicator 80 contained on or in the closure member 50. Indicator 50 may be conventionally sewn, molded or formed, printed, dyed or laminated into or onto the member 50. The indicator 80 is seen to have central section 81, having opposed transverse sections 82 extending therefrom. Extending longitudinally in an opposed manner are the longitudinal sections 85 and 87. Section 87 is seen to be thicker than section 85. The indicator 80 allows the surgeon to determine the location of the patch with respect to the patient after insertion by aligning the respective axes of the tissue repair patch 10 with respect to the patient and the incision, allowing for more precise fixation, either using a tacking instrument or using surgical sutures for affixation. Such directional indicators may be used with other embodiments of the tissue repair patches of the present invention.

Figure 6:
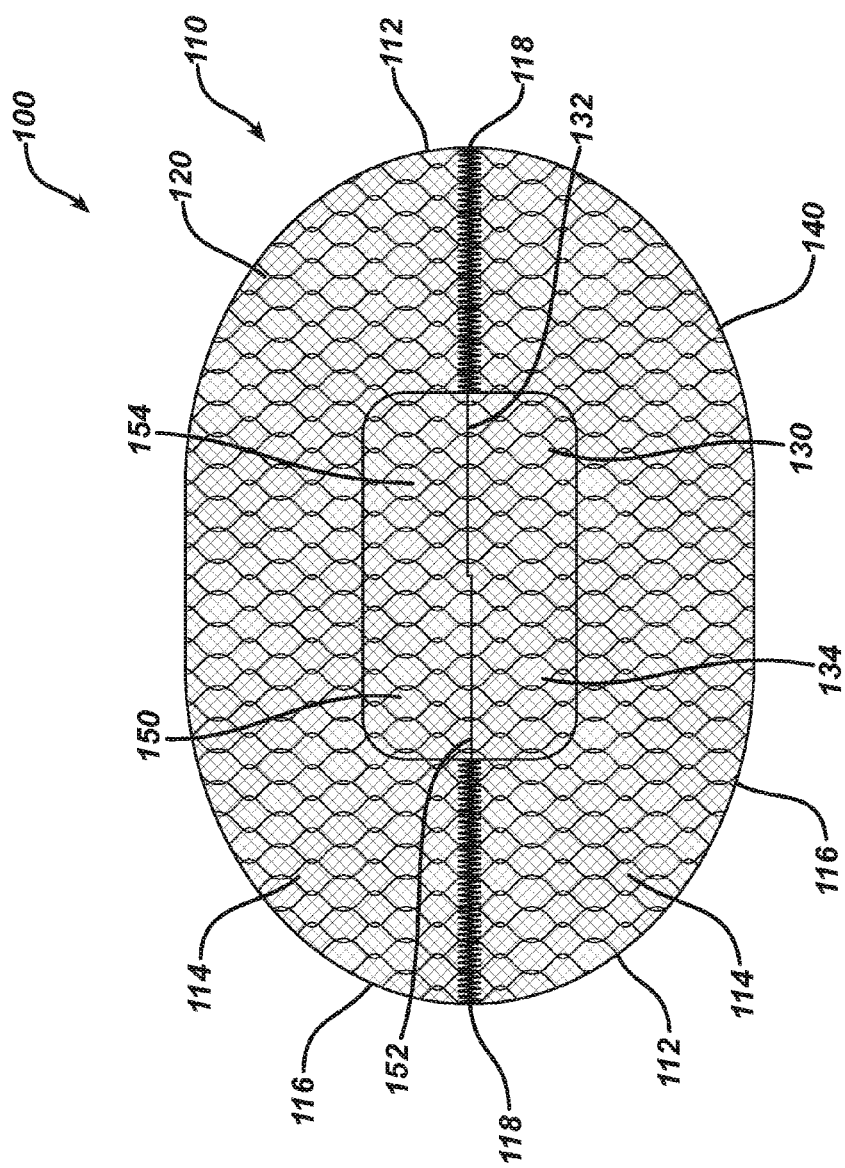
FIG. 6 is a plan view of a tissue repair patch of the present invention made by joining the two halves seen in FIG. 5; the flaps are in the at rest position.
Figure 7:
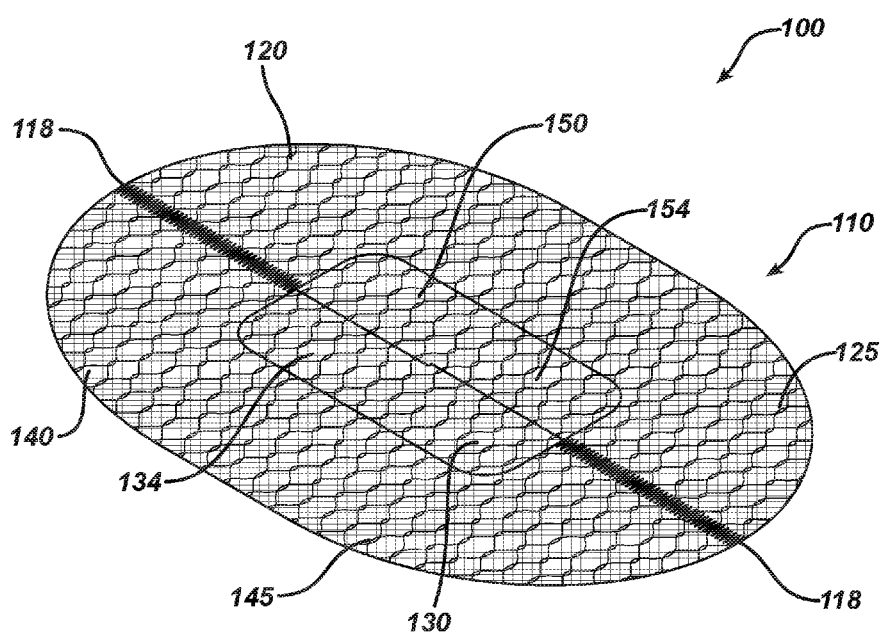
FIG. 7 is a perspective view of the tissue repair patch of FIG. 6; the flaps are in the at rest position.
Figure 8:
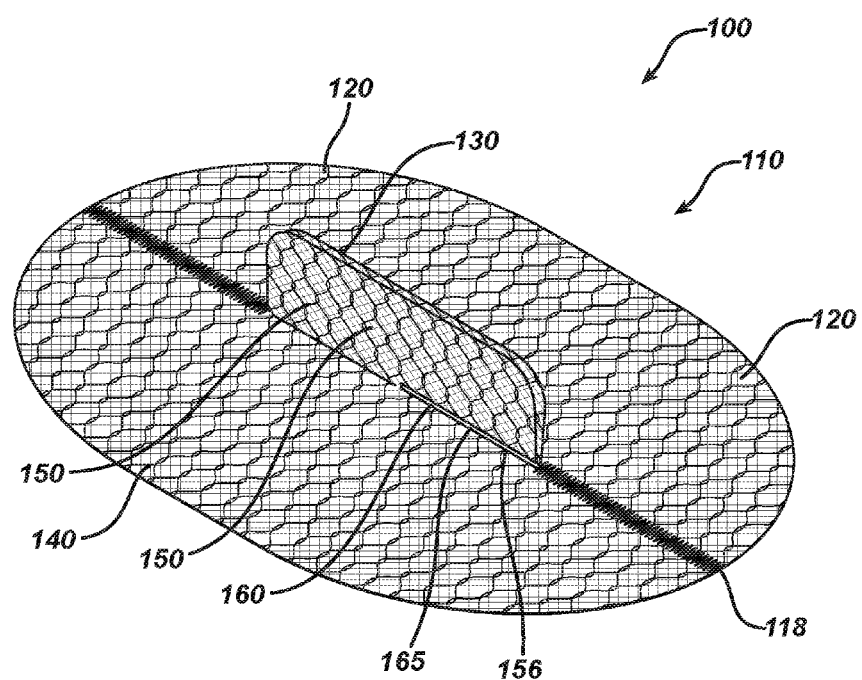
FIG. 8 is a perspective view of the tissue repair patch of FIG. 7 showing both of the flaps in the up position, uncovering the opening in the base member, thereby providing access through the base member.
Figure 9:
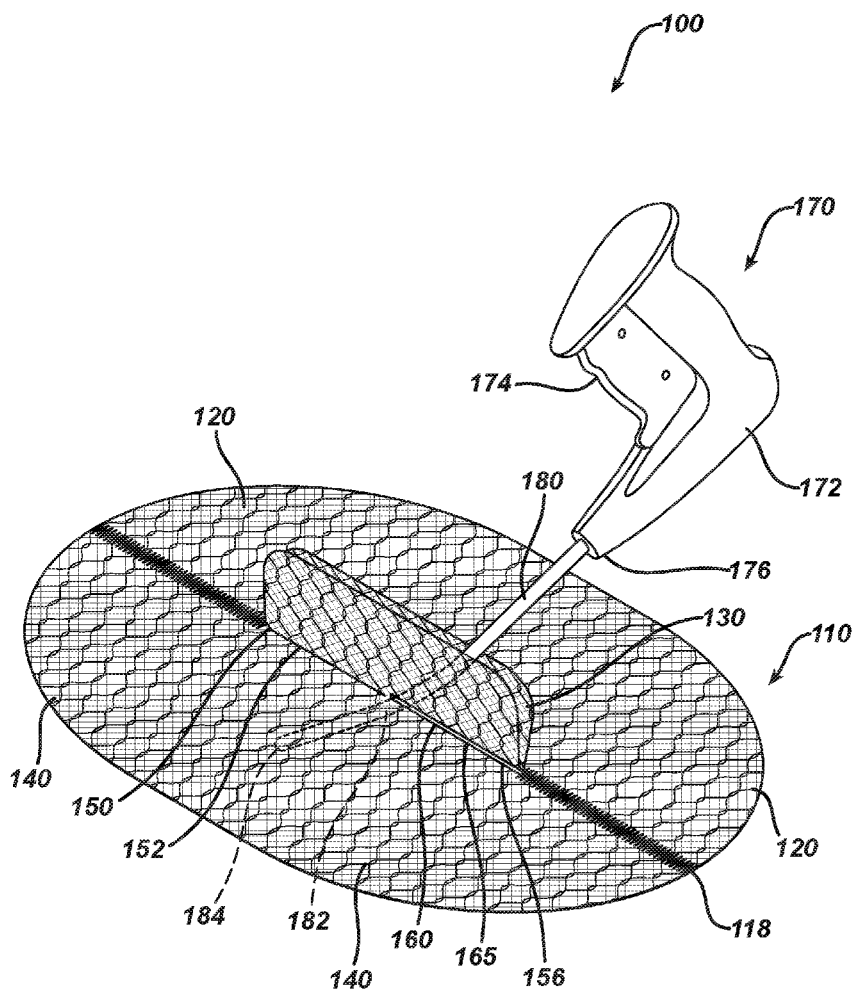
FIG. 9 illustrates the tissue repair patch of FIG. 8 with a curved shaft of a surgical tacking instrument inserted partially through the opening of the base member.

Referring now to FIGS. 5-9, an alternative embodiment of a tissue repair patch 100 of the present invention is seen. The patch 100 is seen to have substantially flat or planar base member 110 formed from substantially flat or planar base sections 120 and 140. The base member 110 has bottom side 112, top side 114 and periphery 116. Base section 120 is seen to have straight side 122 having ends 124. Base section 120 is also seen to have curved side 126 having ends 128 that connect to ends 124. Extending out from straight side 122 is the closure flap member 130 having hinged side 132 and free end 134 separated from side 122 by slot 136. Slot 136 has closed end 137 and open end 138. The closure flap member 130 is seen to have a generally rectangular configuration, but may have other geometric configurations including circular, oval, polygonal, etc., combinations thereof and the like. Base section 140 is seen to have straight side 142 having ends 144. Base section 140 is also seen to have curved side 146 having ends 148 that connect to ends 144. Extending out from straight side 142 is the closure flap member 150 having hinged side 152 and free end 154 separated from side 142 by slot 156. Slot 156 has closed end 157 and open end 158. The closure flap member 150 is seen to have a generally rectangular configuration, but may have other geometric configurations including circular, oval, polygonal, etc., combinations thereof and the like. The base member 110 and the tissue repair patch 100 are formed from the base sections 120 and 140 by connecting the base sections along straight sides 122 and 142 along seams 118. This can be done in any conventional manner including sewing, welding, tacking, stapling, gluing, etc., and combinations and equivalents thereof. It can be seen that only the straight sides 122 and 142 are connected on either side of the closure flap members 130 and 150. The closure flaps members 130 and 150 are mounted together such that hinged side 132 of closure flap 130 is contained in slot 156 of flap member 150 and hinged side 152 of closure flap 140 is contained in slot 136 of closure member 130. This creates the slit 160 in base member 110 having through opening 165 bounded by interior portions of straight sides 122 and 142 of the base sections 120 and 142, respectively, and also bounded by the hinged sides 132 and 152 of the flap members 130 and 150, respectively. In the at rest position as seen in FIG. 6, the flap member 130 rests upon the top side 145 of the base section 140 of base member 110, while the flap member 150 rest upon the top side 125 of base section 120. In this at rest configuration the slit 160 and opening 165 are covered. The tissue repair patch 100 is seen in the ready position in FIG. 8, with the closure flap members 130 and 150 in the upright position exposing the slit 160 and opening so that a fixation instrument can be inserted through the opening 165. A tacking instrument 170 is illustrated in FIG. 9 with tissue repair patch 100 of the present invention. The tacking instrument 170 is seen to have proximal handle 172 and actuation trigger 174. Extending from the distal end 176 of handle 170 is the curved shaft 180 having distal section 182 and distal end 184. The distal section 182 is seen to be inserted through slit 160 and opening 165 between upwardly extending flaps 130 and 150 such that the distal end 184 may be moved about the bottom side 112 of the base member 110 in order to secure the base member to tissue with surgical tacks. Once tacks are placed through the base member 110 of patch 100 to secure the patch 100 to tissue, the tacking instrument 170 may be removed from the slit 160 and the two flap members 130 and 150 can be interlocked by folding or rotating the flap members downwardly onto the top 114 of the base member 110. One or both of the flap members may be optionally bonded or affixed to the base member 110 using various conventional closure methods including adhesives, sutures, surgical fasteners, etc.

Figure 10:
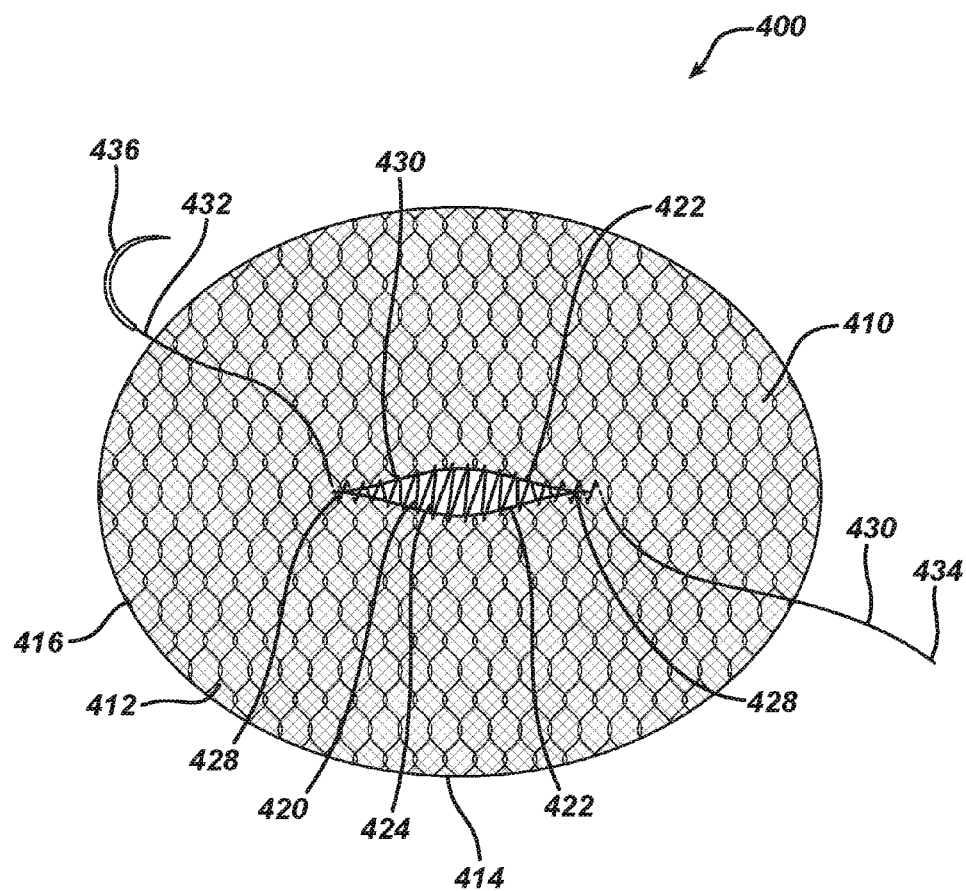
FIG. 10 is a plan view of another embodiment of a tissue repair patch of the present invention; the mesh patch is seen to have an opening with a surgical suture and surgical needle mounted about the opening in a continuous mattress suture configuration.
Figure 11:
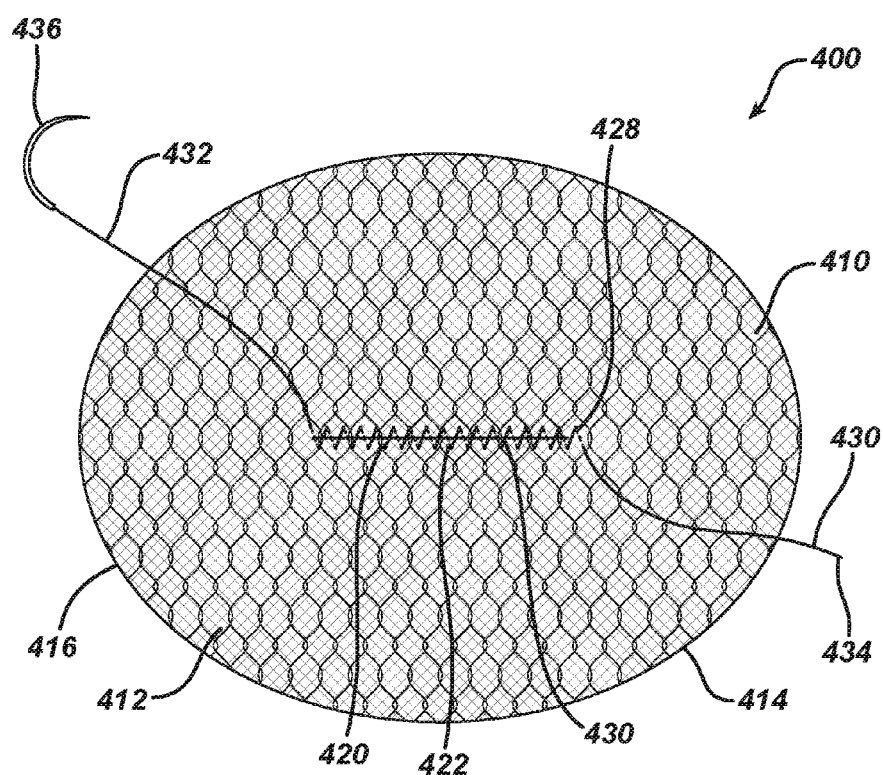
FIG. 11 illustrates the tissue repair patch of FIG. 10, wherein the opening has been closed by applying tension to the suture after the patch has been affixed to the parietal wall of the patient over the hernia defect.
Figure 28:
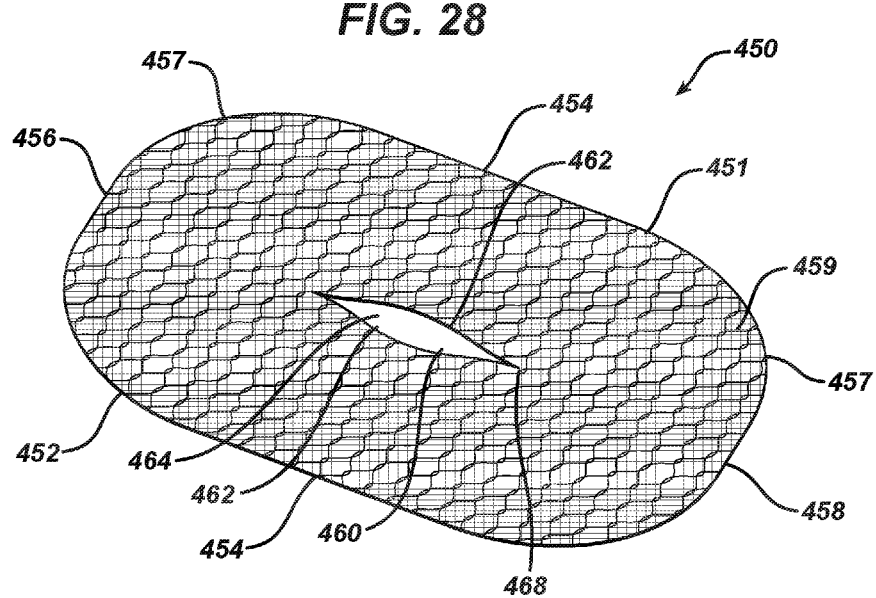
FIG. 28 is a perspective view of an alternate embodiment of a mesh tissue repair patch of the present invention; the patch is seen to have a slit in the base member providing a central opening.
Figure 29:
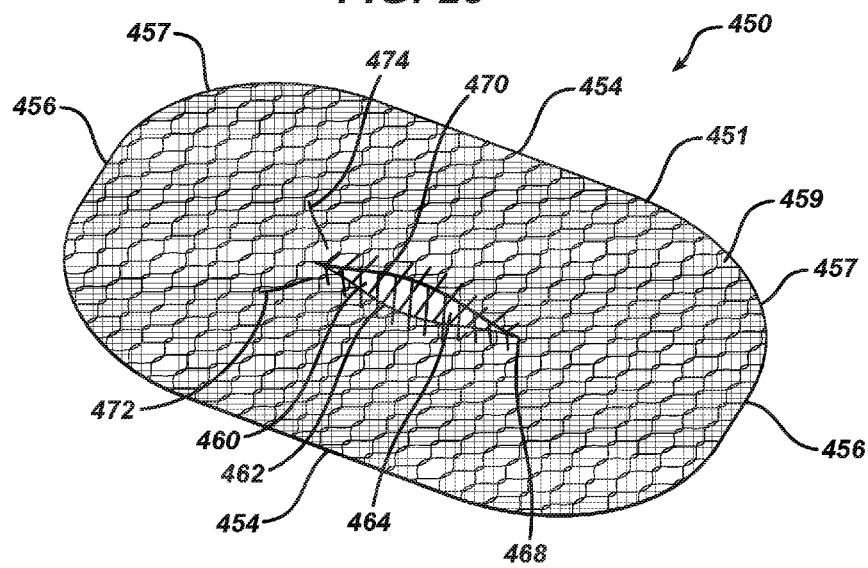
FIG. 29 is a perspective view of the patch of FIG. 28 having a surgical suture mounted about the slit in a shoe lace type configuration to close the opening in the slit.
Figure 30:
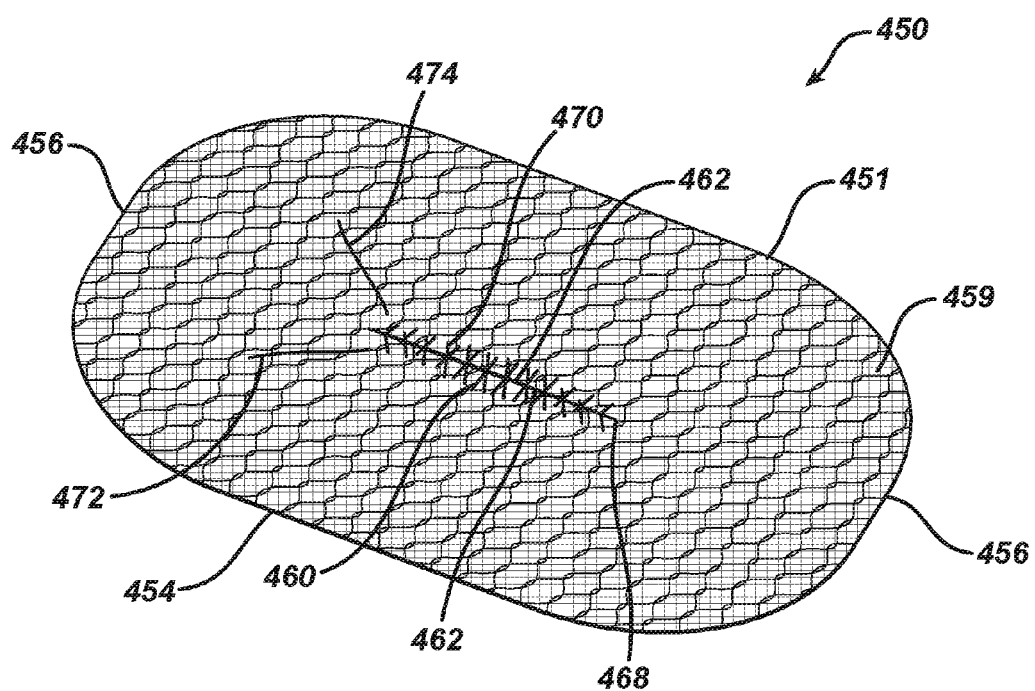
FIG. 30 is a perspective view of the tissue repair patch of FIG. 29, after the suture ends have been tensioned, thereby closing the opening and slit after the patch is secured to the patient's body wall.
Figure 31:
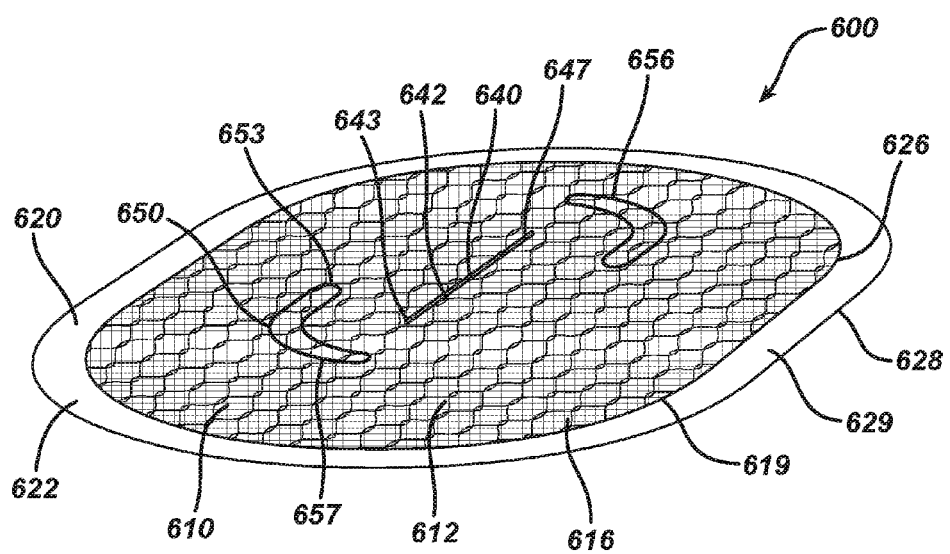
FIG. 31 illustrates a perspective view of a tissue repair patch of the present invention having an adhesion barrier member attached to the bottom side of the base member to form a pocket.

An alternate embodiment 400 of a single plane tissue repair patch of the present invention is seen in FIGS. 10 and 11. The repair patch 400 has a base member 410 having a top side 412 and a bottom side 414. The patch has a periphery 416. Located in the base member 410 is a slit 420 having an opening 424 bounded by sides 422. The slit 420 has ends 428. Mounted about the slit 420 is a surgical suture 430 having ends 432 and 434 and surgical needle 436 mounted to end 432, and optionally, although not shown, to end 434. The suture 430 is mounted about the opening 424 in a conventional mattress suture (continuous) configuration. As seen in FIG. 11, the opening 424 is closed by tensioning the suture ends 432 and 434, causing the sides 422 to approximate. If desired, the suture needles 436 can be used to engage tissue with the suture 430. Referring to FIGS. 28 and 29, a variation of suture mounting is illustrated. The repair patch 450 is similar to repair patch 400, but has a rectangularly shaped base member 451 having opposed major sides 454 and opposed minor sides 456 connected by rounded corners 457. The base member 451 has bottom side 458 and top side 459, and outer periphery 452. The base member 451 has centrally located slit 460 having an opening 464 bounded by sides 462. The slit 460 has ends 468. Mounted about the slit 460 is a surgical suture 470 having ends 472 and 474. The suture 470 is mounted in a "shoe lace" type configuration. The suture 470 is seen to be mounted to slit 460 by engaging opposed sides 462 of slit 460 about the opening 464. Suture 470 is seen to have ends 472 and 474 located adjacent to one another along one end 468 of slit 460. The slit 460 is secured after placement of the patch 450 by pulling on ends 472 and 474 thereby closing opening 464. The suture 460 may optionally have surgical needles mounted to one or both of the ends 472 and 474. The base members 410 and 451 may have any suitable geometric configuration.

Figure 12:
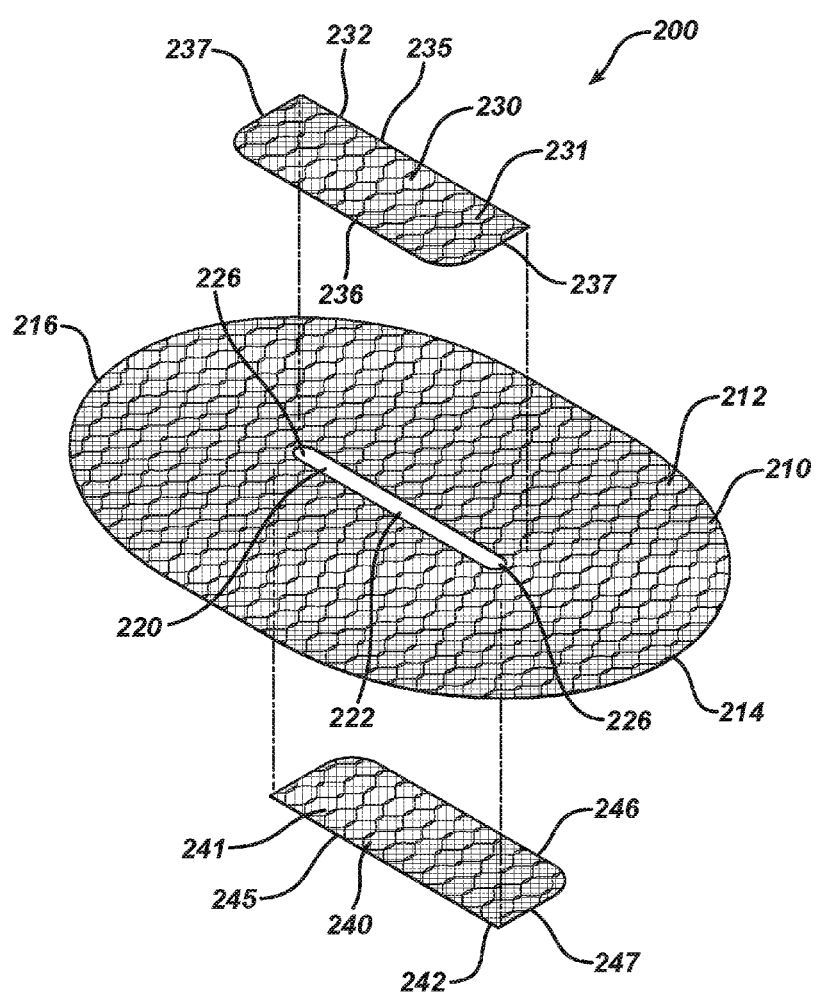
FIG. 12 is an exploded perspective view of another preferred embodiment of a tissue repair patch of the present invention; the patch is seen to have an upper closure flap and a lower closure flap mounted about an opening in the base member.
Figure 13:
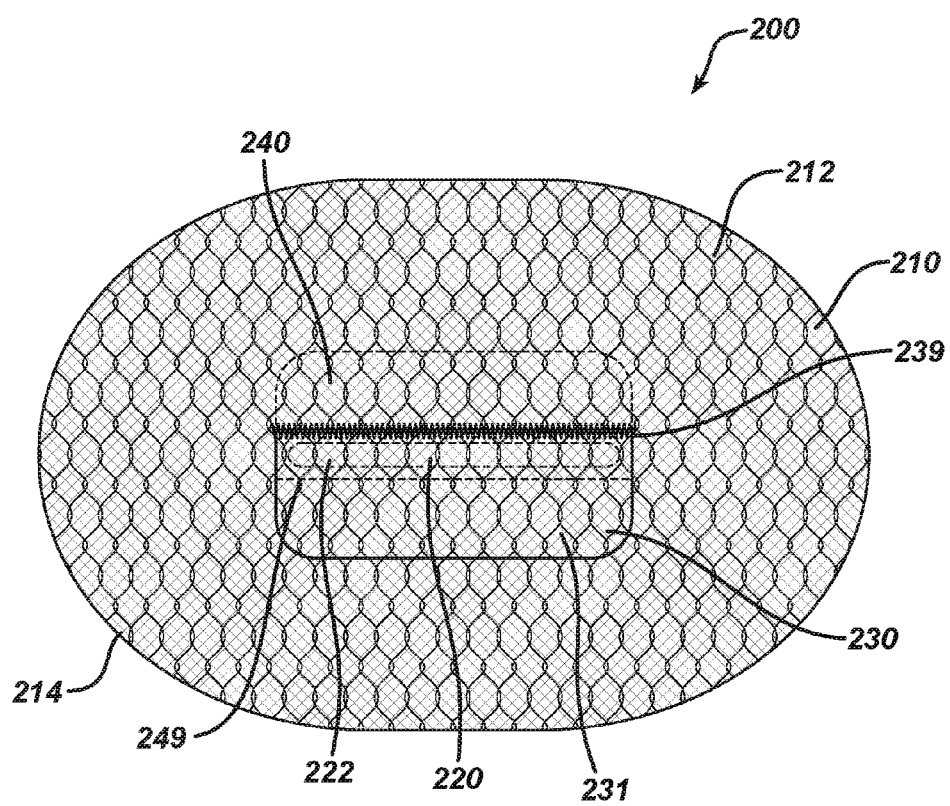
FIG. 13 is a plan view of the tissue repair mesh of FIG. 12, showing the closure flaps mounted about the opening in the base member with one closure flap adjacent to the bottom side of the base member and one closure flap adjacent to the top side of the base member; the flaps are in an at rest position.
Figure 15:
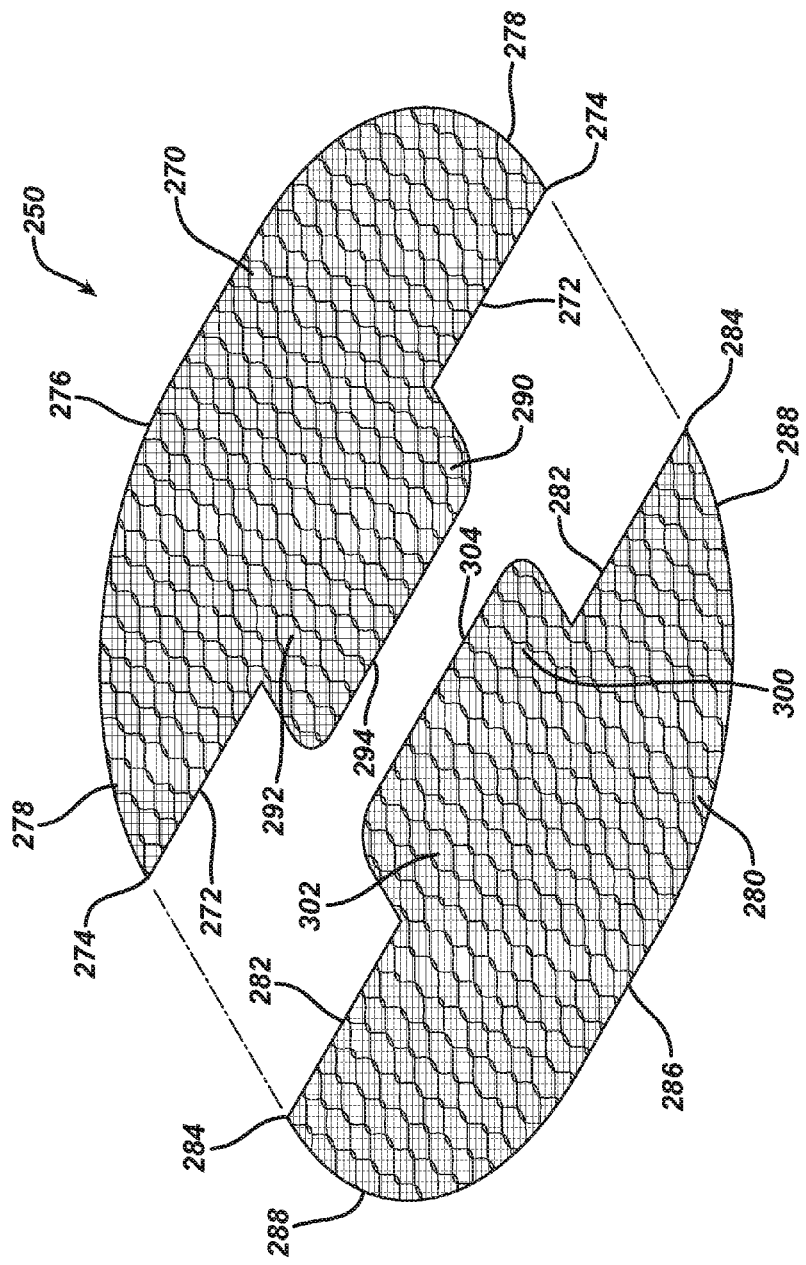
FIG. 15 is an exploded perspective view of two base member halves of the tissue repair patch of FIG. 14; both halves have a closure flap member extending from the base member sections.

A preferred embodiment of a tissue repair patch 200 of the present invention is seen in FIGS. 12 and 13. The patch 200 is seen to have a substantially flat or planar base member 210 having a top 212, bottom 214 and periphery 216. The base member 210 is seen to have an oval shape, but may have other geometric shapes including rectangular, circular, square, polygonal, combinations thereof and the like. Located in the base member 210 is the slot 220 having opening 222 therethrough. Slot 220 is bounded by opposed sides 224 and 225 and curved ends 226. The patch 200 is seen to have upper closure flap 230 and lower closure flap 240. Upper closure flap 230 is seen to have a substantially rectangular shape, although it may have other geometric configurations including circular, oval, rectangular, polygonal, etc., and the like. Flap 230 is seen to have top side 231 and bottom side 232. The flap 230 also has opposed sides 235 and 236 connected by opposed end sides 237. The flap 230 is mounted to the top side 212 of base member 210 adjacent to side 224 of slot 220 by connecting the flap 230 along its side 235 in a conventional manner such as sewing, gluing, stapling, welding, riveting and the like to create a seam 239. In this manner, the flap 230 has its bottom side 232 facing the top side 212 of base member 210, and is positioned to cover slot 220 and opening 222 in the at rest position. The closure flap may be rotated upwardly about seam 239 to uncover slot 220 and opening 222. Mounted to the bottom side 214 of base member 210 is the other closure flap 240. Flap 240 is seen to have top side 241 and bottom side 242. The flap 240 also has opposed sides 245 and 246 connected by opposed end sides 247. The flap 240 is mounted to the bottom side 214 of base member 210 adjacent to side 225 of slot 220 by connecting the flap 240 along its side 245 in a conventional manner such as sewing, gluing, stapling, welding, riveting and the like to create a seam 249. In this manner, the flap 240 has its top side 241 facing the bottom side 214 of base member 210, and is positioned to cover slot 220 and opening 222 in the at rest position. The closure flap may be rotated downwardly about seam 249 to uncover slot 220 and opening 222. The flap 240 may also be rotated upwardly about seam 249 through slot 220 and opening 222.

Figure 16:
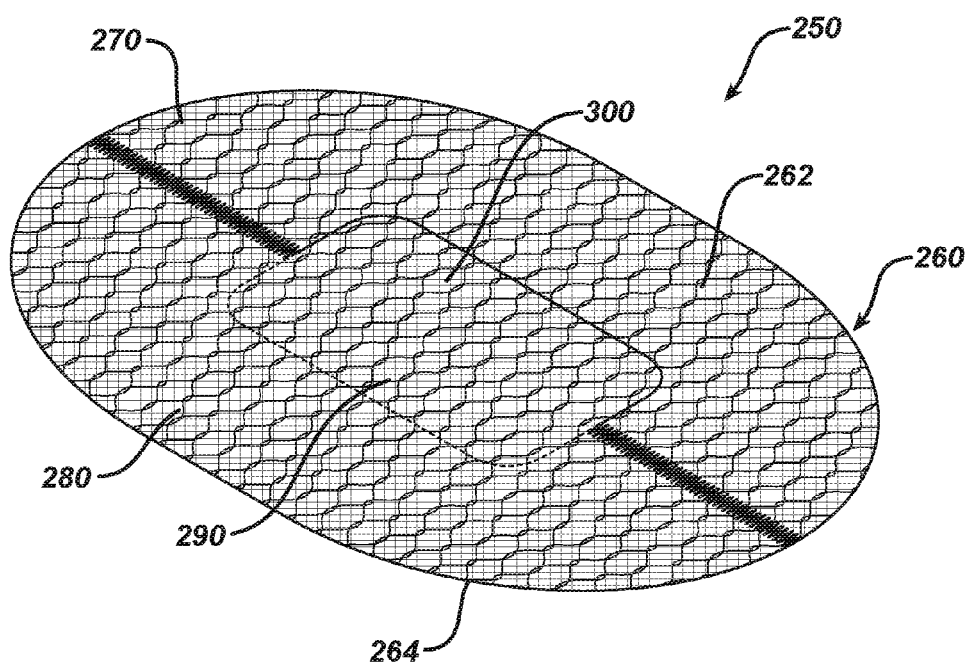
FIG. 16 is a perspective view of the tissue repair patch made by joining together the two halves seen in FIG. 15; one closure flap is positioned below the base member and one closure flap is positioned above the base member.

Referring now to FIGS. 14, 14a, 14b, and 15-17, a preferred tissue repair patch 250 of the present invention is seen. The patch 250 is similar to patch 200, but is constructed in a different manner from two separate base section members. The patch 250 is seen to have substantially flat or planar base member 260 formed from substantially flat or planar base sections 270 and 280. The base member 260 has bottom side 264, top side 262 and periphery 266. Base section 270 is seen to have straight side 272 having ends 274. Base section 270 is also seen to have side 276 having curved ends 278 that connect to ends 274. Extending out from straight side 272 is the closure flap member 290 having hinged side 292 and free side 294. The closure flap member 290 is seen to have a generally rectangular configuration, but may have other geometric configurations including, circular, oval, rectangular, polygonal, etc. and the like. Base section 280 is seen to have straight side 282 having ends 284. Base section 280 is also seen to have side 286 having curved ends 288 that connect to ends 284. Extending out from straight side 282 is the closure flap member 300 having hinged side 302 and free side 304. The closure flap member 300 is seen to have a generally rectangular configuration, but may have other geometric configurations including circular, oval, rectangular, polygonal, etc., and the like. The base member 260 and the hernia closure patch 250 are formed from the base sections 270 and 280 by connecting the base sections along straight sides 272 and 282 along seams 268. This can be done in any conventional manner including sewing, welding, tacking, stapling, gluing, etc., and combinations and equivalents thereof. It can be seen that the straight sides 272 and 282 are connected on either side of the closure flap members 290 and 300, thereby creating a slit 310 between the members 290 and 300 having an opening 315. The slit 310 is bounded by the hinged sides 292 and 302 of the closure flap members 290 and 300 and has opposed ends 312. When assembling the patch 250 and base member 260, closure flap 290 is inserted through opening 315 in slit 310. In the at rest position as seen in FIGS. 12 and 16, the flap member 300 rests upon the top side of the base section 270 of base member 260, while the flap member 290 rests upon the bottom side of base section 280. In the at rest state, closure flaps 290 and 300 each cover the slit 310 and opening 315. It will be appreciated that either closure flap may be rotated through the slit 310 and opening 315, although patch 250 as illustrated shows closure flap member 290 rotated though the slit and resting adjacent to the bottom side 264 of base member 260. In addition, slit 310 may have other geometric configurations and shapes including a slot, etc.

Figure 19:
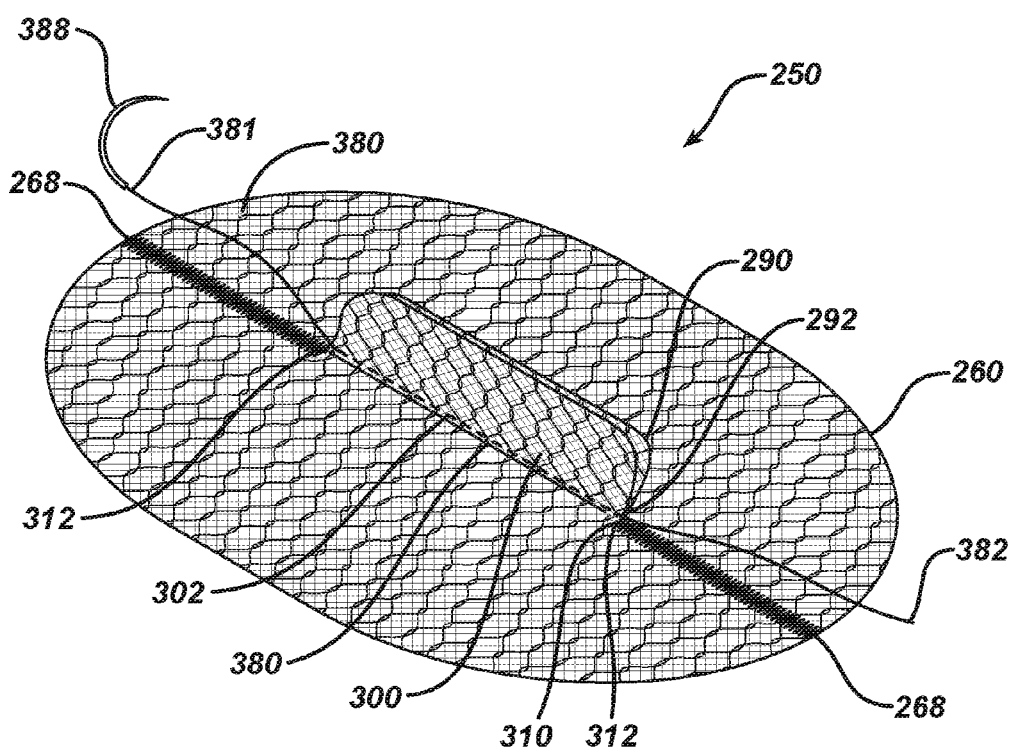
FIG. 19 is a perspective view of the tissue repair patch of FIG. 18, with both flaps optionally sutured together in an upward extending position to close the opening in the base member after the patch has been affixed to tissue.
Figure 20:
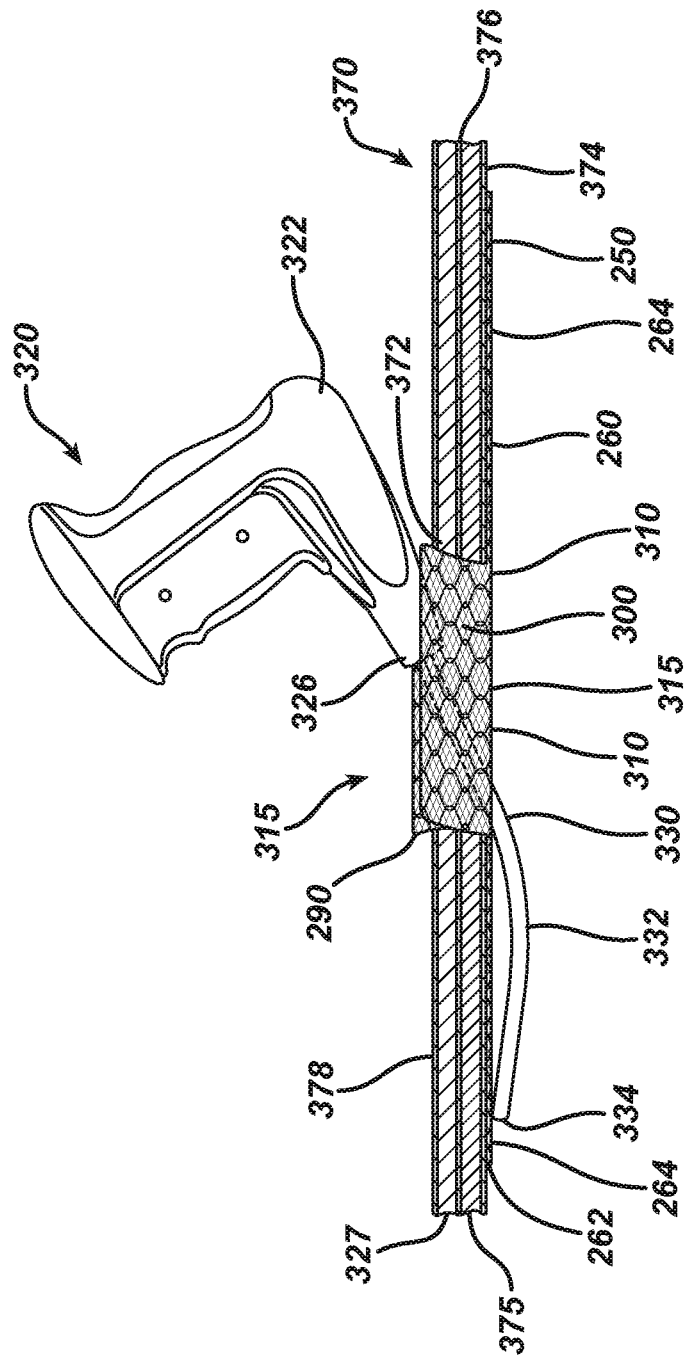
FIG. 20 is a cross-sectional side view of the tissue repair patch of FIG. 16 inserted into the abdominal cavity of a patient and positioned adjacent to the patient's peritoneum; a curved shaft of a surgical tacking instrument is seen inserted thorough an access opening such as a hernia defect in the patient's body wall and through the opening in the base member of the repair patch, such that the distal end of the shaft is in position below the patch to secure a section of the base member of the patch with a tack to the body wall.

Referring now to FIGS. 17-22, the repair patch 250 is seen in a ready position for securement to tissue in a tissue repair procedure such as a hernia repair procedure. As seen in FIG. 17, the patch has been placed in a ready position by rotating flap 300 upwardly away from the top 262 of base member 260. Flap 290 is also seen to be rotated upwardly through slit 310 and opening 315. By rotating closure flaps 290 and 300 in this manner, the slit 310 and opening 315 are uncovered, providing access to a surgical instrument, such as a tacking instrument, or the surgeon's fingers. A surgical tacking instrument 320 is seen in FIG. 18 along with tissue repair patch 250 of the present invention. The tacking instrument 320 is seen to have proximal handle 322 and actuation trigger 324. Extending from the distal end 326 of handle 322 is the curved shaft 330 having distal section 332 and distal end 334. The distal end section 332 is seen to be inserted through slit 310 and opening 315 between upwardly extending closure flaps 290 and 300 such that the distal end 334 may be moved about the bottom side 264 of the base member 260 in order to secure the base member 260 to tissue with surgical tacks. The hernia patch 250 is seen implanted in a patient in FIG. 20. A cross-section of a body wall 370 having a surgically created opening 372 is seen. The body wall 370 is seen to have an inner peritoneal layer 374, a next upper fascia layer 375, a next muscle layer 376, a fat layer 377, and finally a top dermal layer 378. The top side 262 of base member 260 is seen to be mounted adjacent to the peritoneal layer 334, with the closure flap members 290 and 300 extending out and through the opening 332. Shaft 330 of tacking instrument 320 is seen inserted through surgical opening 332, through slit 310 and opening 315 and into the patient's underlying body cavity. The distal end section 332 and distal end 334 are seen to be positioned adjacent to bottom side 264 of base member 260 in order to attach a section of the base member 260 to the peritoneal layer 374. Referring to FIG. 19, the patch 250 is seen with the flap members 290 and 300 optionally secured along their bottom sides 302 and 292 respectfully by surgical suture 380 having ends 381 and 382. Surgical needle 388 is attached to suture end 281. The sutured flap members close the opening 315 in slit 310. Alternatively, the flap members may be joined or secured together to close the slit 310 by conventional adhesives, surgical fasteners, etc. The flap members 290 and 300 may alternatively be utilized in their at rest position during implantation. The shaft of a tacking instrument would be inserted beneath flap 300 through slit 310 and opening 315 without rotating the flaps upwardly. After securement, the flaps may be left in the at rest position without additional securement of the flaps. The flap 290 would prevent tissue or visceral from moving into slot 310 and opening 315; any pressure against flap 290 would cause it to seal against the bottom side 264 of base member 260, closing off slit 310.

Figure 21:
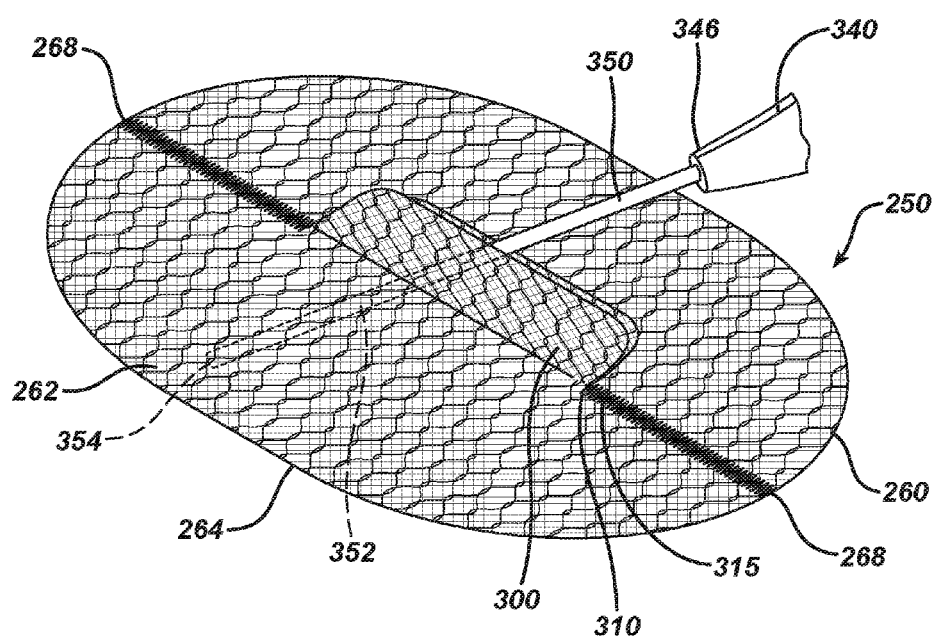
FIG. 21 is a perspective view of the mesh repair patch of FIG. 17, illustrating the distal end of a straight elongated shaft of a surgical tacking instrument partially inserted through the opening of the base member in a position to secure the tissue repair patch to tissue.
Figure 22:
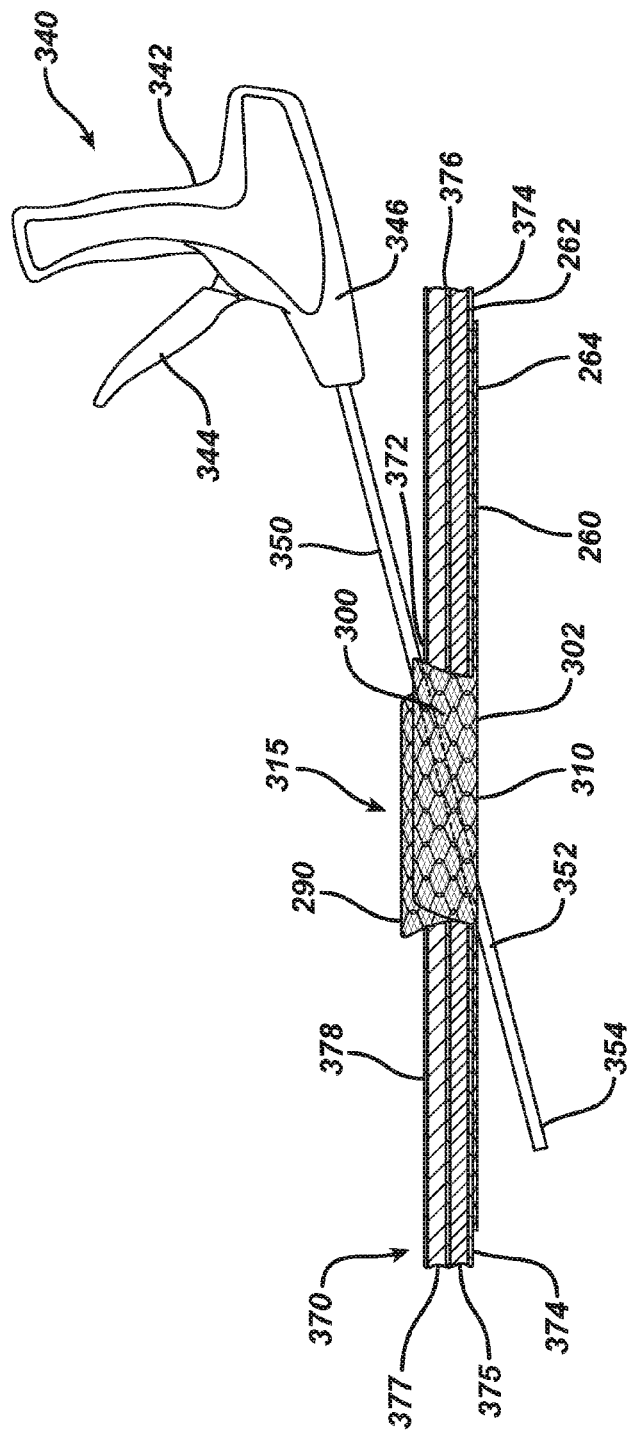
FIG. 22 is a side view of the tissue repair patch of FIG. 21 inserted into the abdominal cavity of a patient and positioned adjacent to the patient's peritoneum; a distal section of a straight shaft of a surgical tacking instrument is seen inserted thorough an access opening in the patient's body wall and through the opening in the base member of the repair patch, such that the distal end of the shaft is in position below the patch to secure a section of the base member of the patch with a tack to the body wall.

A surgical tacking instrument 340 having a straight shaft 350 that can be used to secure a tissue repair patch of the present invention is seen in FIGS. 21 and 22. The instrument 340 has a proximal handle 342 with an actuation trigger 344. Extending from the distal end 346 of handle 340 is the straight shaft 350 having distal section 352 and distal end 354. The distal end section 352 is seen to be inserted through slit 310 and opening 315 between upwardly extending closure flaps 290 and 300 such that the distal end 354 may be moved about the bottom side 264 of the base member 260 in order to secure the base member 260 to tissue with surgical tacks. The tissue repair patch 250 is seen implanted in a patient in FIG. 22. A cross-section of a body wall 370 having a surgically created opening 372 is seen. The body wall 370 is seen to have an inner peritoneal layer 374, a next upper fascia layer 375, a next muscle layer 376, a fat layer 377, and finally a top dermal layer 378. The top side 262 of base member 260 is seen to be mounted adjacent to the peritoneal layer 374, with the closure flap members 290 and 300 extending out and through the opening 332. Shaft 350 of tacking instrument 350 is seen inserted through surgical opening 372, through slit 310 and opening 315 and into the patient's underlying body cavity. The distal end section 352 and distal end 354 are seen to be positioned adjacent to bottom side 264 of base member 260 in order to attach a section of the base member 260 to the peritoneal layer 374.

Figure 23:
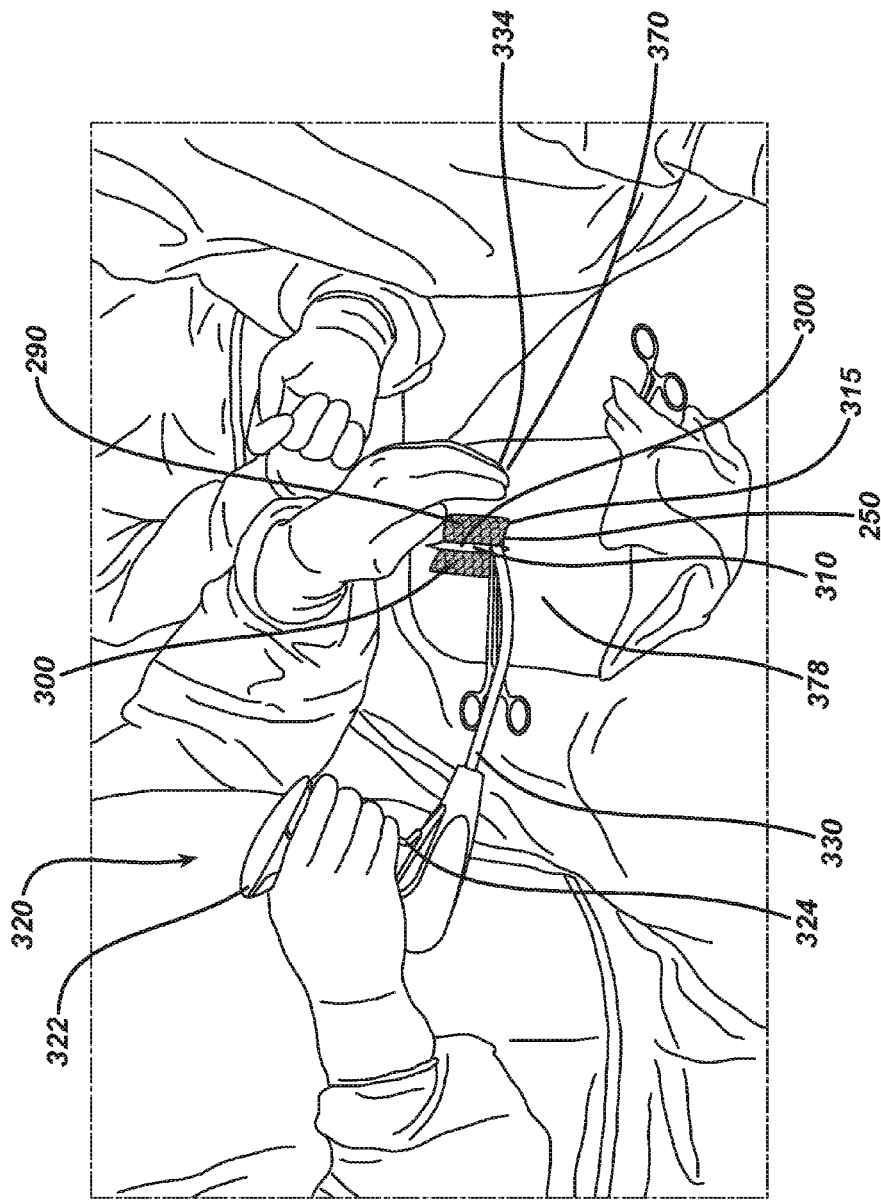
FIG. 23 is an illustration of a hernia repair procedure wherein a surgeon is securing the tissue repair patch of FIG. 17 in position over a hernia defect using a surgical tacking instrument having a curved elongated shaft; the distal section of the shaft is inserted through an access opening in the patient's body wall and through an opening in the tissue repair patch in order to secure the tissue patch to the peritoneum; the surgeon's hand is seen palpating the abdomen above the distal end of the shaft of the instrument to place a tack in a desired position on the patch.
Figure 24:
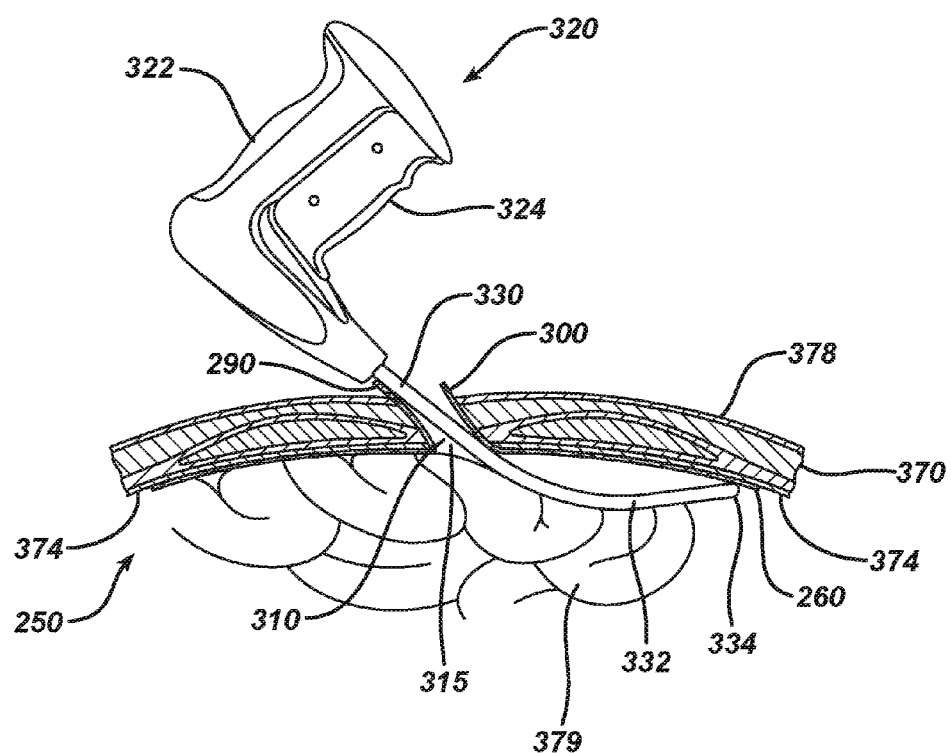
FIG. 24 is a cross-sectional side view illustrating a preferred embodiment of a tissue repair patch of the present invention in place over a hernia defect adjacent to a patient's peritoneum; a curved elongated shaft of a surgical tacking instrument has been positioned through an access opening in the patient's body wall and through an opening in the patch to attach a section of the base member of the patch to the peritoneum; the patient's visceral organs are seen positioned adjacent to the bottom side of the patch and the peritoneum, and the closure flaps are seen to extend upwardly through the opening in the body wall.
Figure 26:
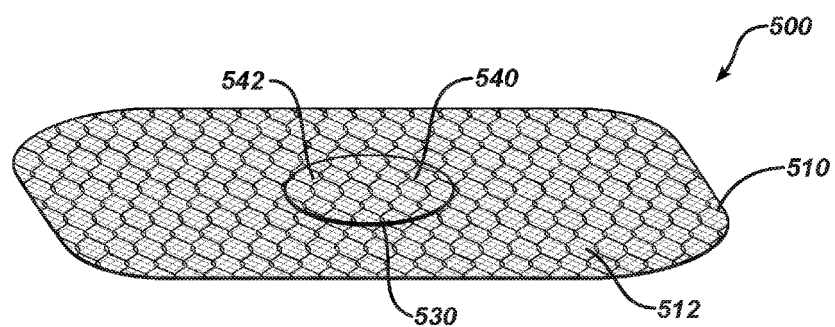
FIG. 26 is a perspective view of the tissue repair patch of FIG. 25 showing the patch secured to the base member.
Figure 27:
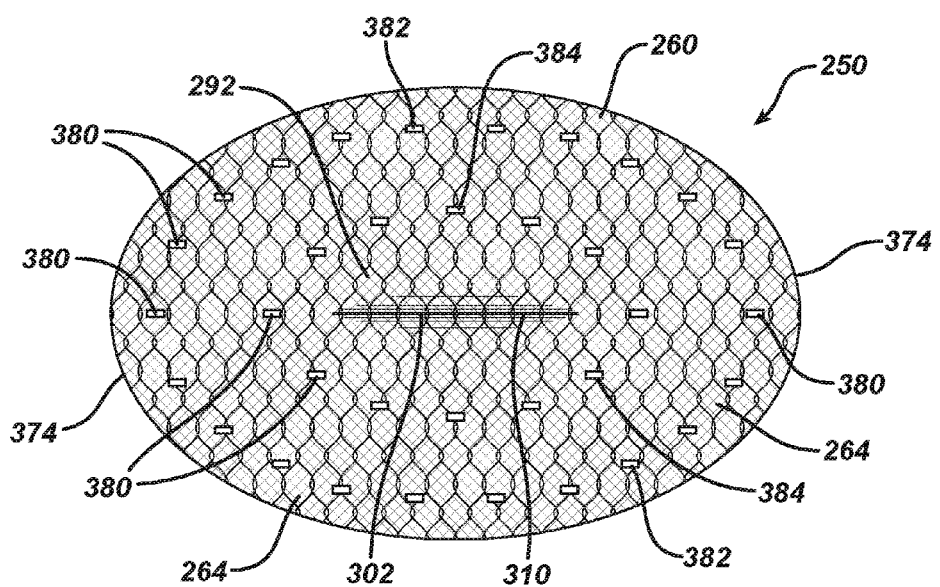
FIG. 27 illustrates a peritoneal view of the bottom side of a preferred embodiment of a tissue repair patch of the present invention secured to the peritoneum with a double row of surgical tacks referred to as a double crown technique; the opening in the base member is seen to be closed, and both flaps have been positioned upwardly away from the top of the base member; the flaps are secured to close the opening in the base member.

FIGS. 23 and 24 illustrate the implantation of a tissue repair patch 250 of the present invention in a patient during a surgical procedure to repair a hernia defect. The surgeon is seen to be holding the handle 322 of a surgical tacking instrument 320 with one hand while engaging the trigger 324. The instrument has a curved shaft 330, and the proximal section 332 of shaft 330 has been placed through opening 372 of body wall 370, and through slit 315 and opening 350 of hernia repair patch 250. Repair patch 250 has been implanted in the patient's body cavity such that the upper side 262 of base member 260 is adjacent to the peritoneal layer 374. The closure flaps 290 and 300 have been rotated upwardly to expose slit 310 and opening 315 and extend out through opening 372 of body wall 370 so that they extend partially above dermal layer 378. The patient's viscera 379 are seen to be adjacent to the bottom side 264 of base member 260. Shaft 330 of tacking instrument 320 is seen inserted through surgical opening 372, through slit 310 and opening 315 and into the patient's underlying body cavity. The distal end section 332 and distal end 334 are seen to be positioned adjacent to bottom side 264 of base member 260 in order to attach a section of the base member 260 to the peritoneal layer 374. The surgeon's other hand is seen to be palpating the patient's body wall 370 above the distal end 334 in order to locate the position of a tack prior to delivering it by actuating trigger 324. Referring to FIG. 26, after implantation of the patch 250 and securement with tacks 380, the bottom side 264 of base member 260 may have two concentric crowns of tacks 382 and 384 to secure the patch 250 to the peritoneal layer 374.

Figure 25:
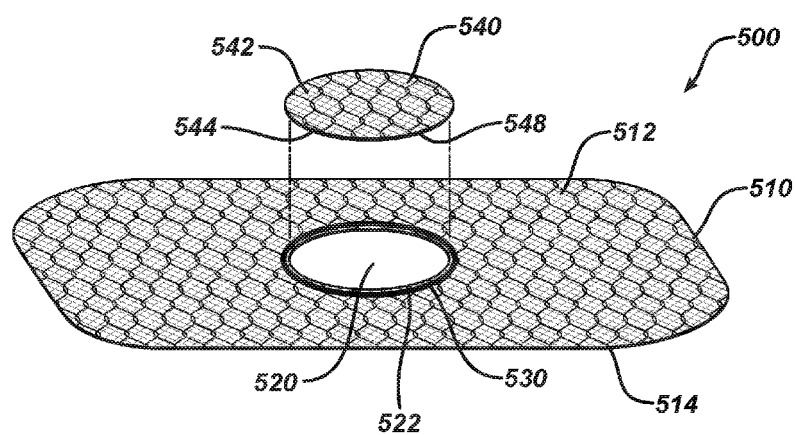
FIG. 25 is an exploded perspective view of an alternate embodiment of a mesh tissue repair patch of the present invention; the base member is seen to have an opening in the base member surrounded by a closure ring, and a closure patch having a mating closure ring is also shown.

Another embodiment of a tissue repair patch of the present invention is seen in FIGS. 25 and 26. The repair patch 500 is seen to have substantially flat base member 510 having top side 512 and bottom side 514. Base member 510 is seen to have circular opening 520 bounded by periphery 522. Closure ring 530 is seen to be mounted about periphery 522 of circular opening 520. The patch 500 also has closure patch 540 having top side 542 and bottom side 544. Mounted to the bottom side 544 of patch 540 is mating closure ring 548. Mating closure ring 548 is removeably engageable with closure ring 530. When used in a surgical procedure, the surgeon removes the closure patch 540 from base member 510 thereby exposing opening 520. The base member 510 is then implanted in a body cavity of a patient such that the top side 512 of base member 510 is adjacent to the inner layer of the body cavity such as the peritoneum. The surgeon then inserts a distal section of the shaft of an attachment instrument such as a surgical tacker through opening 520 into the body cavity below bottom side 514 of the base member 510. After the base member 510 has been secured to the inner layer of tissue and the shaft of the securement instrument has been removed, the surgeon mounts the closure patch 540 to the top side 512 of the base member 510 such that the mating closure ring 548 and the closure ring 530 are engaged.

Figure 32:
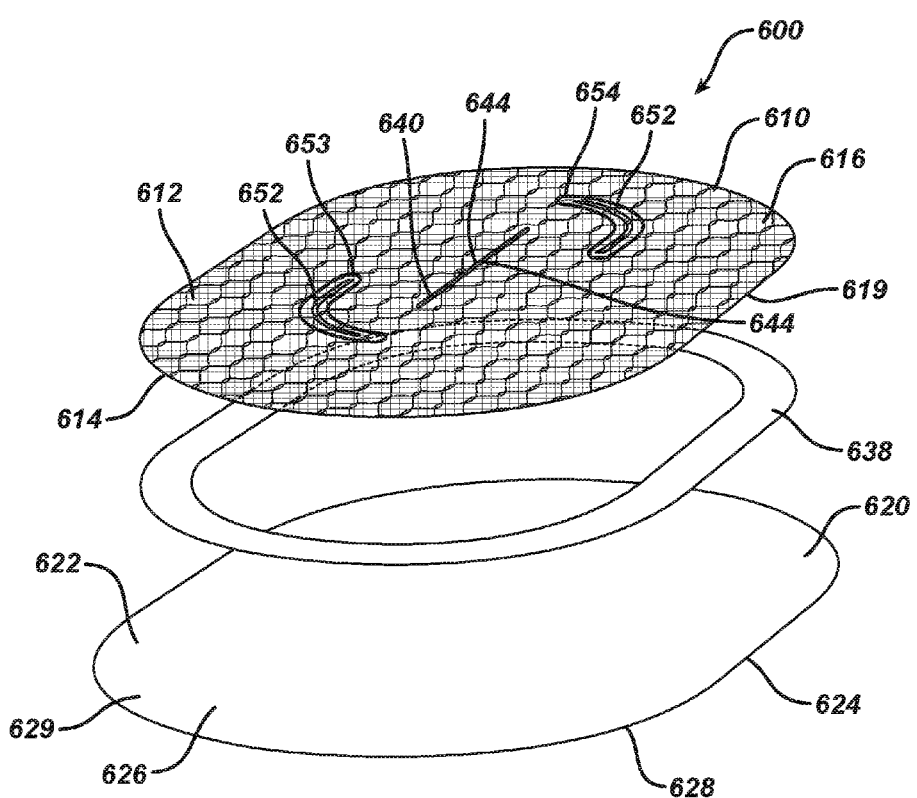
FIG. 32 is an exploded perspective view of the repair patch of FIG. 31.
Figure 33:
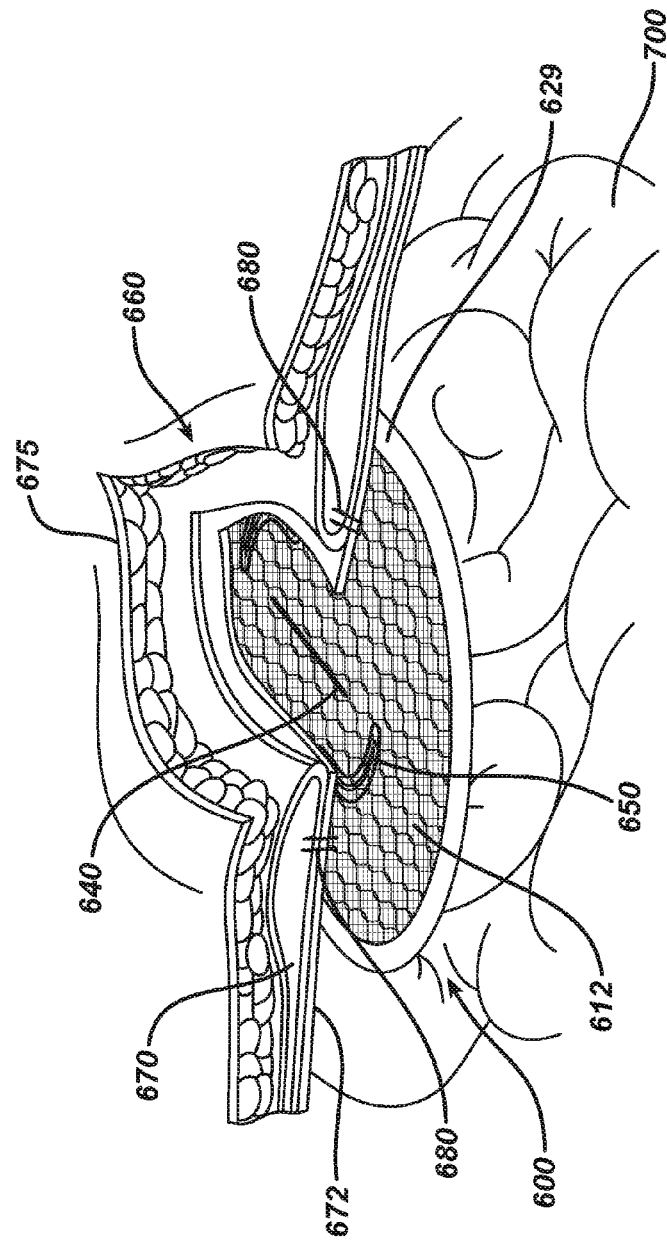
FIG. 33 is a perspective view of the hernia patch of FIG. 31 implanted adjacent to a hernia defect.

Referring to FIGS. 31-37, an additional embodiment of a novel tissue defect repair device 600 of the present invention is illustrated. The device 600 is seen to have a base member 610 having top side 612, bottom side 614 and periphery 616 next to peripheral edge 619. The base member 610 is illustrated having a substantially oval shape or configuration, but may have other configurations including square, rectangular, circular, polygonal, etc, combinations thereof and the like. Although it is preferred that the base member 610 be substantially flat, it may be shaped, for example, curved, etc. Extending through the base member 610 is the centrally located slot 640 having opening 642 bounded by opposed sides 644 and opposed ends 643. The slot 640 is seen to be surrounded by optional sew line 647. If desired, the slot 640 may be located such that it is offset from center. The base member 610 is also seen to optionally have a pair of opposed, offset curved slots 650 having openings 652 bounded by opposed sides 654 and opposed ends 653. The slots 650 are seen to be surrounded by optional sew lines 657. Mounted to the bottom side 614 of base member 610 is the adhesion barrier member 620. Adhesion barrier member 620 is preferably a substantially planar member made from a bioabsorbable polymer having anti-adhesion properties, although if desired the barrier member 620 may be curved or otherwise shaped. The adhesion barrier member 620 is seen to have top side 622, bottom side 624 and periphery 626 and peripheral edge 628. The adhesion barrier member 620 is secured to the bottom side 614 of the base member 610 about the respective peripheries 616 and 626 of the respective members 610 and 620 in order to form a pocket 630 between the bottom side 624 of the base member 610 and the top side 622 of the adhesion barrier member 620. The pocket 30 has periphery 31. The adhesion barrier member 620 may be secured to base member 610 by a variety of conventional methods including but not limited to gluing, welding, bonding, sewing, mechanical fasteners, etc. The pocket 630 is accessible by a surgical instrument such as a surgical tacker (typically by the distal end of the elongated shaft of such an instrument or tacker) through the slot 640 or the optional slots 650. As seen in FIG. 32, the adhesion barrier member is mounted to the base member 610 by a thin polymer film in the form of a ring 638 that is heated to serve as a glue between the two members 610 and 620 to form the structure of the repair device 600 having accessible pocket 630. An example of such a polymer that can be used for ring 638 is polydioxanone. The adhesion barrier member 620 may optionally have a section of the periphery 626 extend radially beyond the peripheral edge 619 of the base member 610 to from a flange section 629 having peripheral edge 628. Referring now to FIG. 33, the tissue repair patch 600 is seen to be implanted in patient below a hernia defect 660 in a body wall 670. Surgically created opening 675 is contained in body wall 670 above the hernia defect 660. The bottom side 624 of the adhesion barrier member is seen to be adjacent to the patient's viscera 700, while the top side 612 of the base member 610 is adjacent to the interior side 672 of body wall 670. The device 600 is seen to have been partially secured to the body wall 670 by surgical tacks 680. The tacks 680 are applied by inserting a distal section of a shaft of a surgical tacking instrument into one of the openings 640 or 650, and locating the periphery 616 of the base member 610 with the distal tip of the distal section of the shaft, and then firing the tacks through the base member 610 into the body wall 670. The periphery 631 of the pocket 630 assists the surgeon in finding and locating the periphery 616 of the base member 610 for proper placement of the tacks 680 or other securement devices. The openings 640 and 650 are secured and closed with an appropriate closure member as described herein, such as sutures.

Figure 34:
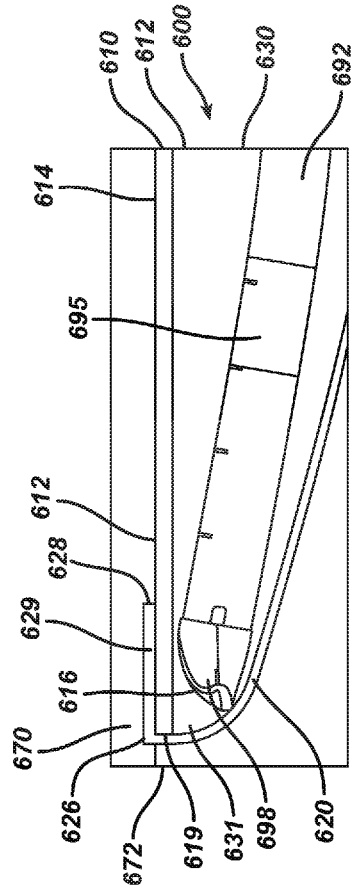
FIG. 34 is a partial cross-sectional view of an alternate embodiment of a repair patch of the present invention having an adhesion barrier mounted to form a pocket.
Figure 35:
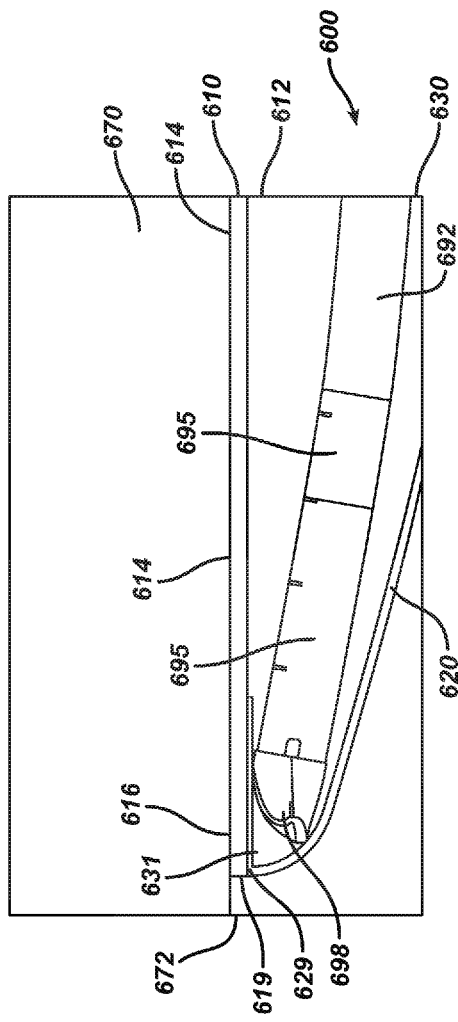
FIG. 35 is a partial cross-sectional view of a repair patch of the present invention in which the adhesion barrier is attached to the bottom side of the base member of the patch about the periphery of the base member.
Figure 36:
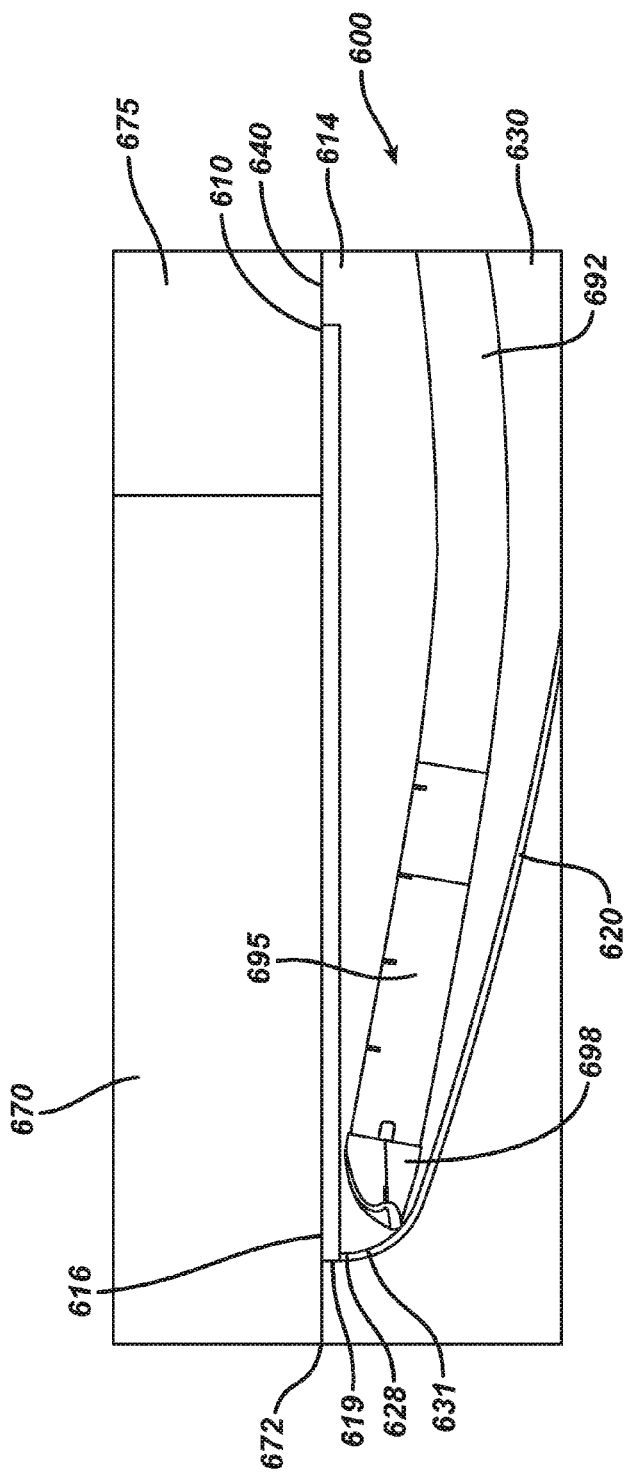
FIG. 36 is a partial cross-sectional view of a repair patch of the present invention in which the adhesion barrier is attached to the periphery of the base member of the patch.
Figure 37:
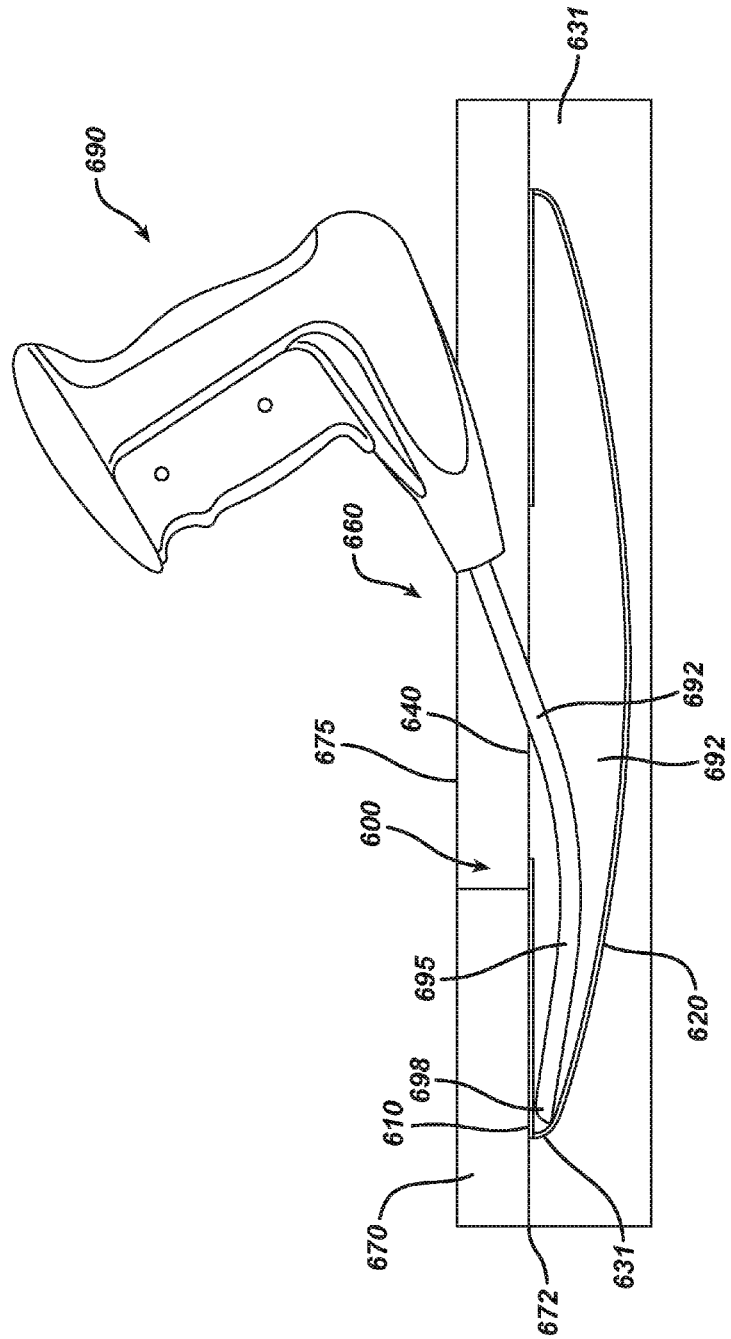
FIG. 37 is a cross-sectional view of the repair patch of FIG. 36 illustrating a tacking instrument with the distal end of the shaft of the instrument in the pocket of the patch, with the distal tip of the instrument adjacent to the periphery of the patch in a position to fire fixation tacks into the tissue of an adjacent body wall.

FIGS. 34-36 illustrate various additional ways in which the adhesion barrier member 620 can be mounted to the base member 610. In FIG. 34, the periphery 626 of the adhesion barrier 620 is moved over and about the peripheral edge 619 of the base member 610 such that the flange section 629 is on the top side 612. The distal tip 698 of the distal section 695 of shaft 692 of a surgical tacking instrument 690 is seen in the pocket 630 in position to fire surgical tacks through the base member 610 and flange section 629 into body wall 670. FIG. 35 illustrates an alternate embodiment of repair patch 600 wherein the flange section 629 of adhesion barrier 620 is mounted to the bottom side 614 of base member 610 about the periphery 616. Another embodiment of repair patch 600 without a flange member 629 is seen in FIG. 36, wherein the periphery 626 of the adhesion barrier member 620 is mounted directly to the periphery 616 of base member 610 adjacent to peripheral edge 619 of the base member 610, or may be mounted directly to edge 619, such that the respective peripheral edges 619 and 628 are substantially coextensive; if desired, the periphery 626 of adhesion barrier 629 may be mounted so as to cover the peripheral edge 619 of base member 610. Referring to FIG. 37, a tissue defect repair device 600 is seen to be placed immediately adjacent to the interior side 672 of a body wall 670 under a hernia defect 660. A surgical tacking instrument 690 having a shaft 692 is seen in proximity to the hernia defect 660 such that a distal section 695 of the shaft 692 is inserted through the opening 675, the defect 60 and through opening 640 of the base member 610. The distal tip 698 of distal end 695 of the shaft 692 is guided into position adjacent to the perhiphery 616 of the base member 610 by the periphery 631 of pocket 630 in order to fire or place tacks or other securement devices to mount the device 600 to body wall 670. The novel repair patch devices 600 of the present invention provide all of the advantages of a single plane construction, while additionally providing a bioabsorbable polymeric adhesion barrier that forms a pocket or pouch to allow the end of a surgical fixation instrument to be inserted into the pocket or pouch and guided into place in order to affix the device to a body wall while protecting the underlying viscera and/or tissue from contact with the device.

The repair patches of the present invention may optionally contain or be coated with sufficiently effective amounts of an active agent such as a therapeutic agent. Substances which are suitable as active agents include conventional agents that may be naturally occurring or synthetic and may include but are not limited to, for example, antibiotics, antimicrobials, antibacterials, antiseptics, chemotherapeutics, cytostatics, metastasis inhibitors, antideabetics, antimycotics, gynaecological agents, urological agents, anti-allergic agents, sexual hormones, sexual hormone inhibitors, haemostyptics, hormones, peptide-hormones, antidepressants, vitamins such as Vitamin C, antihistamines, naked DNA, plasmid DNA, cationic DNA complexes, RNA, cell constituents, vaccines, and cells occurring naturally in the body or genetically modified cells.

In one embodiment, the active agents may be antibiotics including such agents as gentamicin or ZEVTERA™ (ceftobiprole medocaril) brand antibiotic (available from Basilea Pharmaceutica Ltd., Basel Switzerland). In one embodiment, an implant may include broadband antimicrobials used against different bacteria and yeast (even in the presence of bodily liquids) such as octenidine, octenidine dihydrochloride (available as active ingredient Octenisept® disinfectant from Schulke & Mayr, Norderstedt, Germany as), polyhexamethylene biguanide (PHMB) (available as active ingredient in Lavasept® from Braun, Switzerland), triclosan, copper (Cu), silver (Ag), nanosilver, gold (Au), selenium (Se), gallium (Ga), taurolidine, N-chlorotaurine, alcohol based antiseptics such as Listerine® mouthwash, N a-lauryl-L-arginine ethyl ester (LAE), myristamidopropyl dimethylamine (MAPD, available as an active ingredient in SCHERCODINE™ M), oleamidopropyl dimethylamine (OAPD, available as an active ingredient in SCHERCODINE™ O), and stearamidopropyl dimethylamine (SAPD, available as an active ingredient in SCHERCODINE™ S). In one embodiment, the agent may be octenidine dihydrochloride (hereinafter referred to as octenidine) and/or PHMB.

Although it is preferred to have a single, centrally located opening in the hernia repair patch devices of the present invention, the opening and associated closure member may be offset from the center. Additionally, more than one opening and closure member may be utilized in the hernia repair devices of the present invention.

The following examples are illustrative of the principles and practice of the present invention, although not limited thereto.

Example 1

A patient with a ventral or incisional hernia is prepared for an open hernia repair procedure in the following manner. The skin area surrounding the hernia is scrubbed with a conventional antimicrobial solution such as betadine. The patient is administered conventional general anesthesia in a conventional manner by induction and inhalation. The surgeon then initiates the surgical procedure by making an incision in the skin and subcutaneous tissue overlying the hernia. In the case of planned intra-peritoneal mesh placement, the hernia sac is opened. The edges of the healthy fascia around the defect are examined and any attachments of the viscera to the abdominal wall are divided to create a free space for fixation of the mesh.

At this point in the procedure, the surgeon then prepares a mesh tissue repair device, configured as a hernia patch, of the present invention having closure flaps and a base member with an opening and an attached adhesion barrier forming a pocket for insertion through the abdominal wall defect and into the abdominal cavity such that the top side of the mesh is adjacent to the peritoneum surrounding the defect, and the bottom side of the mesh device is facing down toward the patient's viscera. Stay sutures may be placed through the mesh into the abdominal tissue as desired, i.e. at the four compass points of the mesh (North, South, East, West). The flaps are rotated upwardly after placement to expose the opening in the base member of the mesh. The mesh is fixated with a conventional surgical tacker or tacking instrument or other means of fixation. At least a section of the tacker is inserted through the opening such that the distal end of the tacker is in the pocket created between the mesh and the bottom side of the base member, and the surgeon locates the periphery of the repair device by locating the tip of the distal end of the instrument adjacent to the periphery of the pocket. The perimeter of the mesh is then fixated using a plurality of tacks in a crown configuration. The tacker is removed from the pocket and the opening in the mesh is closed by folding the flaps as appropriate for the present invention. The flaps may be optionally secured using adhesive, suture, rivets, or other closure means, or may be returned to their at rest position without securement to each other. The hernia defect may be primarily closed if desired. The skin incision is closed using appropriate suturing or closure techniques, and the incision is appropriately bandaged and the patient is moved to a recovery room.

The novel hernia repair devices of the present invention have numerous advantages. The novel repair patch devices provide a single layer mesh repair device that can be affixed via tacking in an open intraperitoneal hernia repair procedure. The repair patch devices have additional advantages including less foreign material (i.e., lower mass of foreign material) and the ability to implant a single layer tissue repair mesh in open procedures. The tissue repair devices of the present invention, preferably made from mesh, may potentially accelerate the rate of tissue integration, provide less area for biofilm formation, have a lower cost of manufacture, and are easier to package, sterilize, and use with improved ergonomics. A peripherally attached adhesion barrier provides a pocket for containing a distal end of surgical instrument, thereby isolating the viscera from the instrument. The adhesion barrier is optionally removable.

Although this invention has been shown and described with respect to detailed embodiments thereof, it will be understood by those skilled in the art that various changes in form and detail thereof may be made without departing from the spirit and scope of the claimed invention.

We claim:

1. A single plane tissue defect repair device for repairing a tissue defect in a body wall, comprising:
    a substantially flat single plane base member having a top tissue-facing side, a bottom viscera-facing side, an outer periphery and a peripheral edge, wherein the base member is a single mesh layer;
    an access opening located in said base member and extending through the base member from the top side to the bottom side;
    a closure member associated with said opening adapted to prevent tissue or viscera from moving through the opening, said closure member having a first position such that the access opening is covered and underlying tissue or viscera is prevented from moving through the access opening and a second position such that the access opening is uncovered wherein a surgical instrument can be inserted therethrough; and,
    a polymeric, bioabsorbable adhesion barrier member having a top side, a bottom side, an outer periphery, and a peripheral edge, said adhesion barrier mounted to the base member about their respective outer peripheries such that a pocket is formed between the top side of the adhesion barrier and the bottom side of the base member, said pocket accessible through the opening,
    wherein the base member is configured to be affixed to tissue from the bottom viscera-facing side.

2. The tissue repair device of claim 1, wherein the base member additionally comprises a polymeric layer.

3. The device of claim 2, wherein the polymeric layer comprises a nonabsorbable polymer.

4. The device of claim 2, wherein the polymeric layer comprises a bioabsorbable polymer.

5. The device of claim 4, wherein the polymer is selected from the group consisting of silicone, PTFE, polyester, and polypropylene.

6. The device of claim 5, wherein the bioabsorbable polymer is selected from the group consisting of oxidized regenerated cellulose, polydioxanone, poliglecaprone 25 (copolymer of glycolide and epsilon-caprolactone) and combinations thereof.

7. The device of claim 2, wherein the polymeric layer is an adhesion barrier.

8. The tissue repair device of claim 1, wherein the adhesion barrier member is substantially flat.

9. The tissue repair device of claim 1, wherein the adhesion barrier member is curved.

10. The tissue repair device of claim 1, wherein the adhesion barrier member is shaped.

11. The device of claim 1, wherein the base member comprises a mesh.

12. The device of claim 1, wherein the base member comprises a fabric.

13. The device of claim 12, wherein the fabric is woven.

14. The device of claim 12, wherein the fabric is nonwoven.

15. The device of claim 1, wherein the base member comprises an expanded polymeric film.

16. The device of claim 1, wherein the base member comprises a biocompatible, nondegradable polymer.

17. The device of claim 16, wherein the nondegradable polymer is selected from the group consisting of polypropylene, polyester, nylon, and ultra high molecular weight polyethylene.

18. The device of claim 1, wherein the base member comprises a bioabsorbable polymer.

19. The device of claim 18, wherein the bioabsorbable polymer is selected from the group consisting of polylactides, polyglycolides, polydioxanones, polycaprolactones, copolymers of glycolides and trimethylene carbonate, and copolymers of lactides and trimethylene carbonate, and copolymers and blends thereof.

20. The device of claim 1, wherein the base member comprises a biocompatible nondegradable polymer and a bioabsorbable polymer.

21. The device of claim 1, wherein the opening is a slit.

22. The device of claim 1 wherein the opening is circular.

23. The device of claim 1, wherein the opening is slot shaped.

24. The tissue repair device of claim 1, wherein the closure member comprises opposed closure flap members hingingly mounted about the opening.

25. The tissue repair device of claim 1, wherein the closure member comprises a patch having an outer periphery, wherein a section of the periphery is mounted to the top side of the base member about the opening.

26. The tissue repair device of claim 1, wherein the closure member comprises a surgical suture mounted about the opening.

27. The tissue repair device of claim 1, wherein the closure member comprises a patch having a top side and a bottom side with an engagement member extending from the bottom side, and wherein the base member has a mating engagement member mounted to the top side about the opening, such that the closure patch may be engaged and disengaged from the base member.

28. The tissue repair device of claim 1, wherein the opening comprises a slit having opposed sides and the closure member comprises a surgical suture threaded about the slit adjacent to the sides.

29. The device of claim 1, wherein the opening is centrally located.

30. The device of claim 1, comprising at least two openings and closure members.

31. The device of claim 1, wherein the adhesion barrier member comprises a polymer selected from the group consisting of group consisting of oxidized regenerated cellulose, polydioxanone, poliglecaprone 25 (copolymer of glycolide and epsilon-caprolactone) and combinations thereof.

32. The device of claim 1, wherein the adhesion barrier outer periphery extends beyond the outer peripheral edge of the base member to form a radially extending flange.

33. The device of claim 32, wherein the flange is folded over the peripheral edge of the base member and mounted to the outer periphery of the base member on the top side of the base member.

34. The device of claim 32, wherein the flange is folded under the peripheral edge of the base member and mounted to the outer periphery of the base member on bottom side of the base member.

35. The device of claim 1, wherein the adhesion barrier is mounted to the base member such that the peripheral edges are coextensive.

36. The device of claim 1, wherein the adhesion barrier member is mounted to the periphery of the base member such that it covers at least in part the peripheral edge of the base member.

37. The device of claim 1, wherein the pocket has an outer periphery.

38. A method of performing a body wall defect repair in an open surgical procedure, comprising the steps of:
   A. inserting a single plane tissue repair device on an inside layer of a body wall having a tissue defect, wherein the repair device comprises:
   a substantially flat single plane base member having a top tissue-facing side, a bottom viscera-facing side, and an outer periphery, wherein the base member is a single mesh layer;
   an access opening located in said base member and extending through the base member from the top side to the bottom side;
   a closure member associated with said opening adapted to prevent tissue or viscera from moving through the opening, said closure member having a first such that the access opening is covered and underlying tissue or viscera is prevented from moving through the access opening and a second position such that the access opening is uncovered wherein a surgical instrument can be inserted therethrough; and,
   a bioabsorbable adhesion barrier member having a top side, a bottom side and an outer periphery, said adhesion barrier mounted to the base member about their respective outer peripheries such that a pocket having a periphery is formed between the top side of the adhesion barrier and the bottom viscera-facing side of the base member, said pocket accessible through the opening;
   B. positioning the device about the defect such that the top tissue-facing side of the base member is adjacent to the inside layer of the body wall;
   C. moving the closure member to the second position such that the access opening is uncovered and inserting the end of a surgical fixation instrument through the opening to access the pocket and the bottom viscera-facing side of the base member, and guiding the instrument to the periphery of the pocket, and fixating the base member to the inside layer of the body wall through the bottom viscera-facing side of the base member by applying at least one surgical fastener; and,
   D. manipulating the closure member to the first position to close off and cover the opening such that underlying tissue and viscera are prevented from entering the access opening.

39. The method of claim 38, wherein the tissue defect is a hernia.

* * * * *